United States Patent
Nielsen et al.

(10) Patent No.: US 11,332,579 B1
(45) Date of Patent: *May 17, 2022

(54) FUSED DITHIENO BENZOTHIADIAZOLE POLYMERS FOR ORGANIC PHOTOVOLTAICS

(71) Applicant: PHILLIPS 66 COMPANY, Houston, TX (US)

(72) Inventors: Laura Nielsen, Bartlesville, OK (US); Reed Eisenhart, Bartlesville, OK (US); Victoria Suding, Bartlesville, OK (US); Hualong Pan, Bartlesville, OK (US); Alyssa Chinen-Mendez, Bartlesville, OK (US)

(73) Assignee: Phillips 66 Company, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/531,053

(22) Filed: Nov. 19, 2021

(51) Int. Cl.
*C08G 75/06* (2006.01)
*C07D 513/14* (2006.01)

(52) U.S. Cl.
CPC ........... *C08G 75/06* (2013.01); *C07D 513/14* (2013.01)

(58) Field of Classification Search
CPC ............................... C08G 75/06; C07D 513/14
See application file for complete search history.

(56) References Cited

U.S. PATENT DOCUMENTS

| 8,624,232 B2 | 1/2014 | Sonar et al. |
| 9,233,930 B2 | 1/2016 | Kirner et al. |

(Continued)

FOREIGN PATENT DOCUMENTS

| CN | 104086752 | 10/2014 |
| CN | 104119504 | 10/2014 |

(Continued)

OTHER PUBLICATIONS

Lee et al., Macromolecules 2016, 49, 9358-9370.*

*Primary Examiner* — Shane Fang
(74) *Attorney, Agent, or Firm* — Phillips 66 Company

(57) ABSTRACT

A composition comprising:

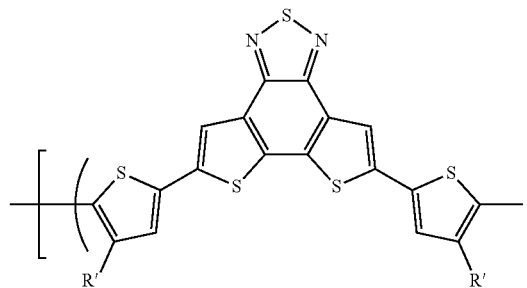

(Continued)

Conventional Device Architecture

Inverted Device Architecture

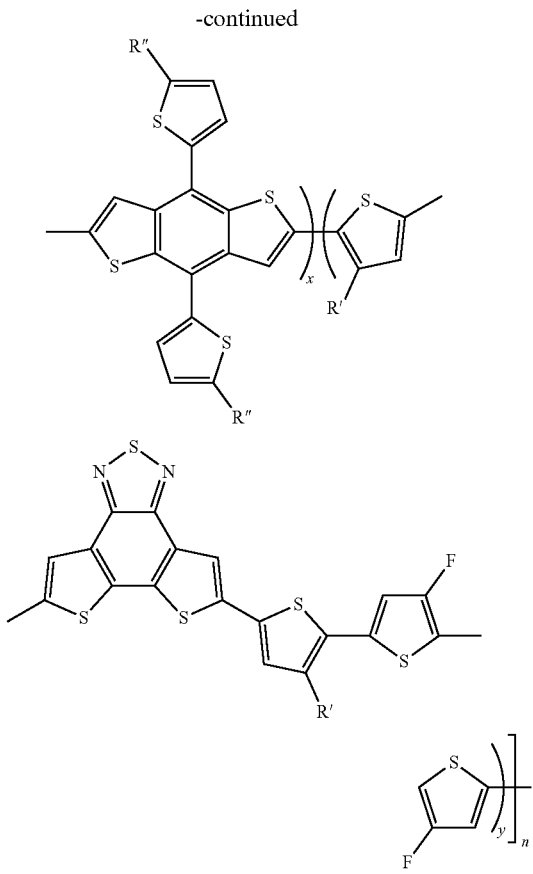

wherein the compositional ratio of x/y ranges from about 1/99 to about 99/1, and n ranges from 1 to 1,000,000. Additionally, in this composition, R' and R" are independently selected from: H, unsubstituted or substituted branched alkyls with 1 to 60 carbon atoms, or unsubstituted or substituted linear alkyls with 1 to 60 carbon atoms.

17 Claims, 9 Drawing Sheets

(56) References Cited

U.S. PATENT DOCUMENTS

| | | |
|---|---|---|
| 9,847,489 B1 | 12/2017 | Shin et al. |
| 2008/0102559 A1 | 5/2008 | Ong et al. |
| 2008/0103286 A1 | 5/2008 | Ong et al. |
| 2010/0179301 A1 | 7/2010 | Henninger et al. |
| 2012/0153274 A1 | 6/2012 | Sonar et al. |
| 2020/0308342 A1 | 10/2020 | Song et al. |

FOREIGN PATENT DOCUMENTS

| | | |
|---|---|---|
| CN | 104211916 | 12/2014 |
| CN | 103483560 | 12/2015 |
| CN | 103483559 | 2/2016 |
| CN | 106967096 | 1/2019 |
| CN | 106589326 | 4/2019 |
| CN | 113087725 | 7/2021 |
| EP | 1615237 | 9/2008 |
| EP | 2762514 | 3/2012 |
| EP | 2774940 | 9/2014 |
| EP | 3009463 | 4/2016 |
| EP | 3260456 | 12/2017 |
| WO | 2005003126 | 1/2005 |
| WO | 2005070992 | 8/2005 |
| WO | 2009115413 | 9/2009 |
| WO | 2009117025 | 9/2009 |
| WO | 2010136401 | 12/2010 |
| WO | 2010138566 | 12/2010 |
| WO | 2011131280 | 10/2011 |
| WO | 2012013310 | 2/2012 |
| WO | 2015013747 | 2/2015 |
| WO | 2015096797 | 7/2015 |
| WO | 2016062258 | 4/2016 |
| WO | 2018065356 | 4/2018 |
| WO | 2020225169 | 11/2020 |
| WO | 2021136435 | 7/2021 |

* cited by examiner

FUSED DITHIENO BENZOTHIADIAZOLE POLYMERS FOR ORGANIC PHOTOVOLTAICS

CROSS-REFERENCE TO RELATED APPLICATIONS

None.

STATEMENT REGARDING FEDERALLY SPONSORED RESEARCH OR DEVELOPMENT

None.

FIELD OF THE INVENTION

This invention relates to polymers for organic photovoltaics.

BACKGROUND OF THE INVENTION

Solar energy using photovoltaics requires active semiconducting materials to convert light into electricity. Currently, solar cells based on silicon are the dominating technology due to their high-power conversion efficiency. Recently, solar cells based on organic materials showed interesting features, especially on the potential of low cost in materials and processing.

Organic photovoltaic cells have many potential advantages when compared to traditional silicon-based devices. Organic photovoltaic cells are light weight, economical in the materials used, and can be deposited on low-cost substrates, such as flexible plastic foils. However, organic photovoltaic devices typically have relatively low power conversion efficiency (the ratio of incident photons to energy generated) and poor film forming ability.

There exists a need for a polymer to create organic photovoltaic cells that has high photovoltaic performance.

BRIEF SUMMARY OF THE DISCLOSURE

A composition comprising:

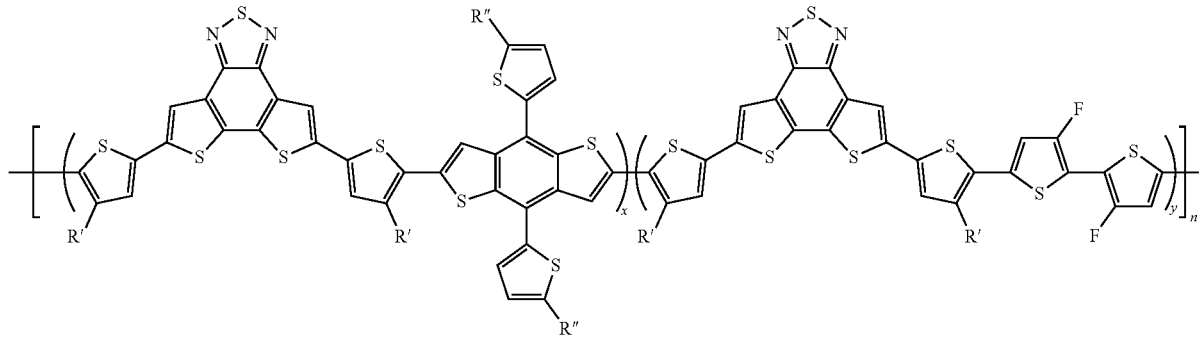

wherein the compositional ratio of x/y ranges from about 1/99 to about 99/1, and n ranges from 1 to 1,000,000. Additionally, in this composition, R' and R" are independently selected from: H, unsubstituted or substituted branched alkyls with 1 to 60 carbon atoms, or unsubstituted or substituted linear alkyls with 1 to 60 carbon atoms.

An alternate composition comprising:

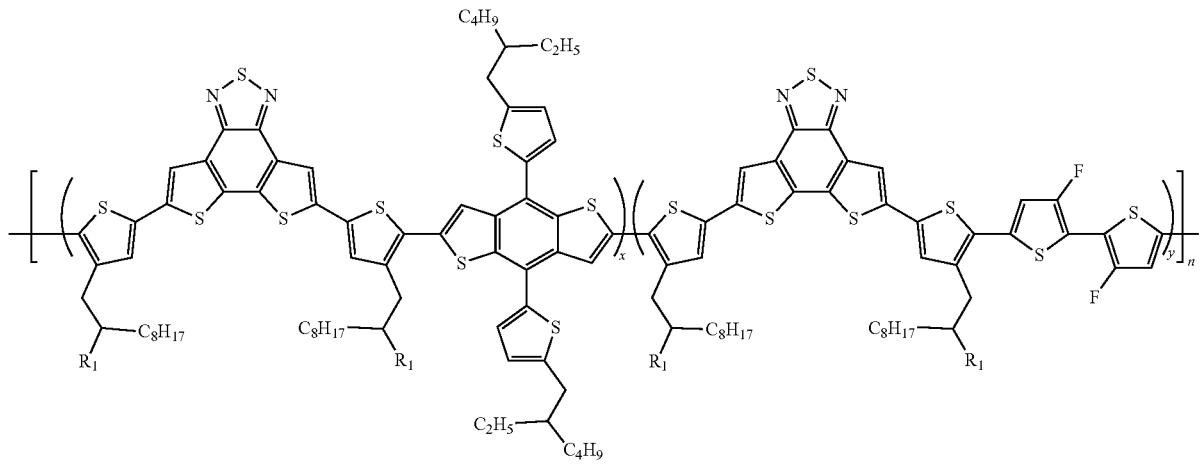

wherein the compositional ratio of x/y ranges from about 1/99 to about 99/1, and n ranges from 1 to 1,000,000. Additionally, in this composition, $R_1$ is selected from: H, unsubstituted or substituted branched alkyls with 1 to 60 carbon atoms, or unsubstituted or substituted linear alkyls with 1 to 60 carbon atoms.

BRIEF DESCRIPTION OF THE DRAWINGS

A more complete understanding of the present invention and benefits thereof may be acquired by referring to the follow description taken in conjunction with the accompanying drawings in which.

DETAILED DESCRIPTION

Figure 1:
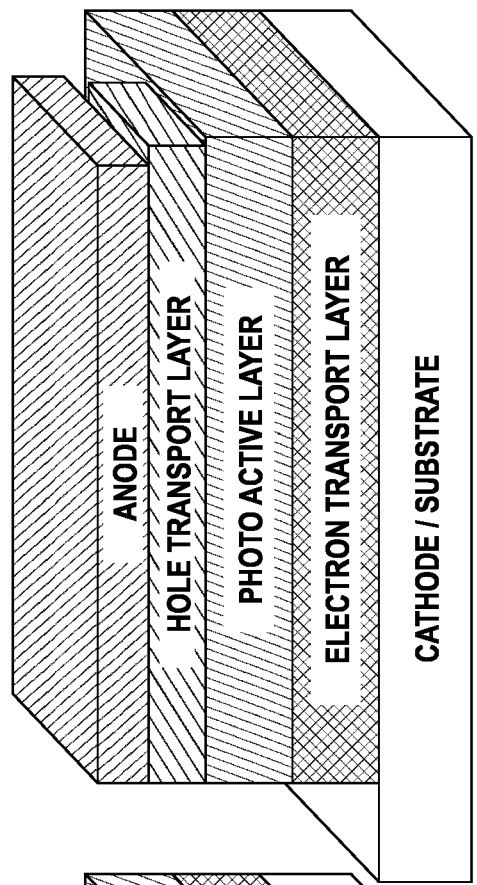
FIG. 1 depicts a conventional device architecture and an inverted device architecture.
Figure 1:
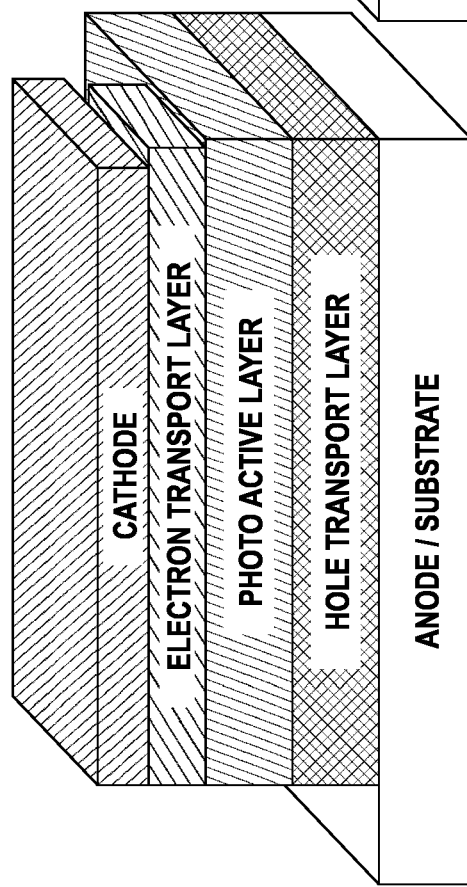

Turning now to the detailed description of the preferred arrangement or arrangements of the present invention, it should be understood that the inventive features and concepts may be manifested in other arrangements and that the scope of the invention is not limited to the embodiments described or illustrated. The scope of the invention is intended only to be limited by the scope of the claims that follow.

"Alkyl," as used herein, refers to an aliphatic hydrocarbon chains. In one embodiment the aliphatic hydrocarbon chains are of 1 to about 100 carbon atoms, preferably 1 to 30 carbon atoms, and includes straight and branched chained, single, double and triple bonded carbons such as methyl, ethyl, n-propyl, isopropyl, n-butyl, isobutyl, sec-butyl, t-butyl, n-pentyl, isopentyl, neo-pentyl, n-hexyl, isohexyl, propenyl, butenyl, pentenyl, hexenyl, butadienyl, pentadienyl, hexadienyl, ethynyl, propynyl, butynyl, pentynyl, hexynyl, 2-ethylhexyl, 2-butyloctyl, 2-hexyldecyl, 2-octyldedodecyl, 2-decyltetradecy and the like. In this application alkyl groups can include the possibility of substituted and unsubstituted alkyl groups. Substituted alkyl groups can include one or more halogen substituents.

"Alkoxy," as used herein, refers to the group R—O— where R is an alkyl group of 1 to 100 carbon atoms. In this application alkoxy groups can include the possibility of substituted and unsubstituted alkoxy groups.

"Aryl" as used herein, refers to an optionally substituted, mono-, di-, tri-, or other multicyclic aromatic ring system having from about 3 to about 50 carbon atoms (and all combinations and subcombinations of ranges and specific numbers of carbon atoms therein), with from about 6 to about 20 carbons being preferred. Non-limiting examples include, for example, phenyl, naphthyl, anthracenyl, and phenanthrenyl. Aryl groups can be optionally substituted with one or with one or more Rx. In this application aryl groups can include the possibility of substituted aryl groups, bridged aryl groups and fused aryl groups. As used herein aryl groups also include heteroaryls, including structures with more than one heteroatom. Non-limiting examples of heteroatoms that can be heteroaryls include B, N, O, Al, Si, P, S, Ge, Bi, Te, Sn, and Se. Some non-limiting examples of aryl groups with heteroaryls include: thiophene, pyridine, pyrrole, furan, stibole, arsole selenophene, imidazole, pyrazole, oxathiole, isoxathiole, thiazole, triazole, thiadiazole, diazine, oxazine, indole, and thiazine.

"Ester", as used herein, represents a group of formula —COOR wherein R represents an "alkyl", "aryl", a "heterocycloalkyl" or "heteroaryl" moiety, or the same substituted as defined above "Ketone" as used herein, represents an organic compound having a carbonyl group linked to a carbon atom such as —C(O)Rx wherein Rx can be alkyl, aryl, cycloalkyl, cycloalkenyl or heterocycle.

"Amide" as used herein, represents a group of formula "—C(O)NR$^x$R$^y$," wherein R$^x$ and R$^y$ can be the same or independently H, alkyl, aryl, cycloalkyl, cycloalkenyl or heterocycle.

The present embodiment describes a composition comprising:

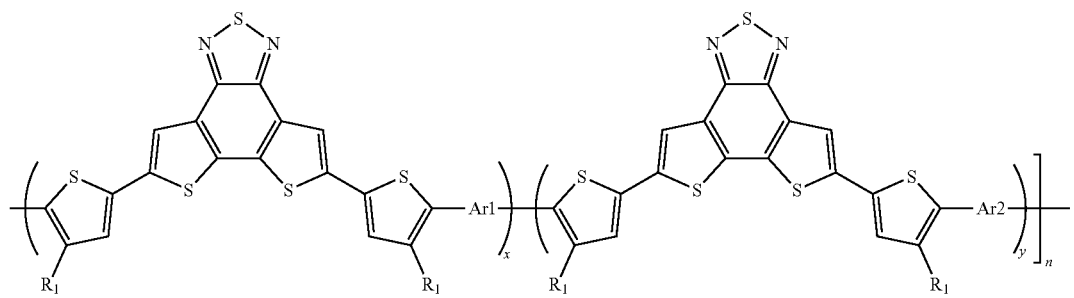

In this embodiment, Ar1 is independently selected from the group consisting of:

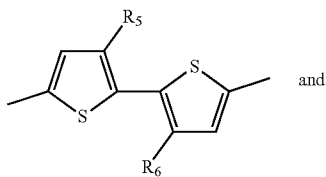

and

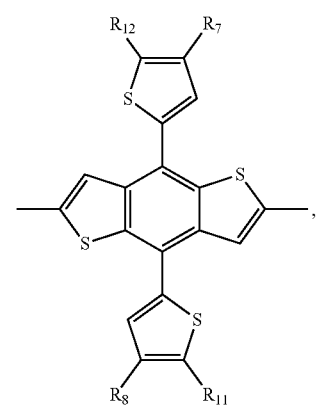

and Ar2 can be selected from

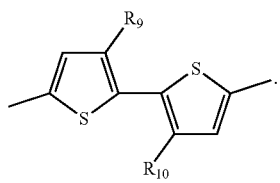

Furthermore $R_1$, $R_5$, $R_6$, $R_7$, $R_8$, $R_9$, $R_{10}$, $R_{11}$, and $R_{12}$ are independently selected from F, Cl, H, unsubstituted or substituted branched alkyls with 1 to 60 carbon atoms, and unsubstituted or substituted linear alkyls with 1 to 60 carbon atoms. In some embodiments,

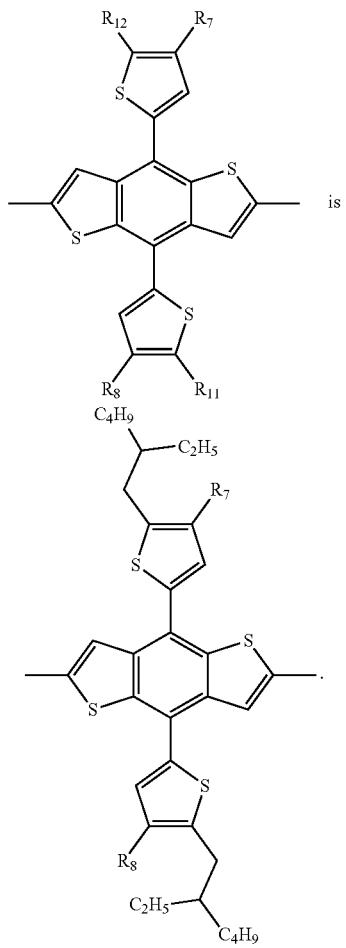

is

In yet another embodiment, the composition can be A composition comprising:

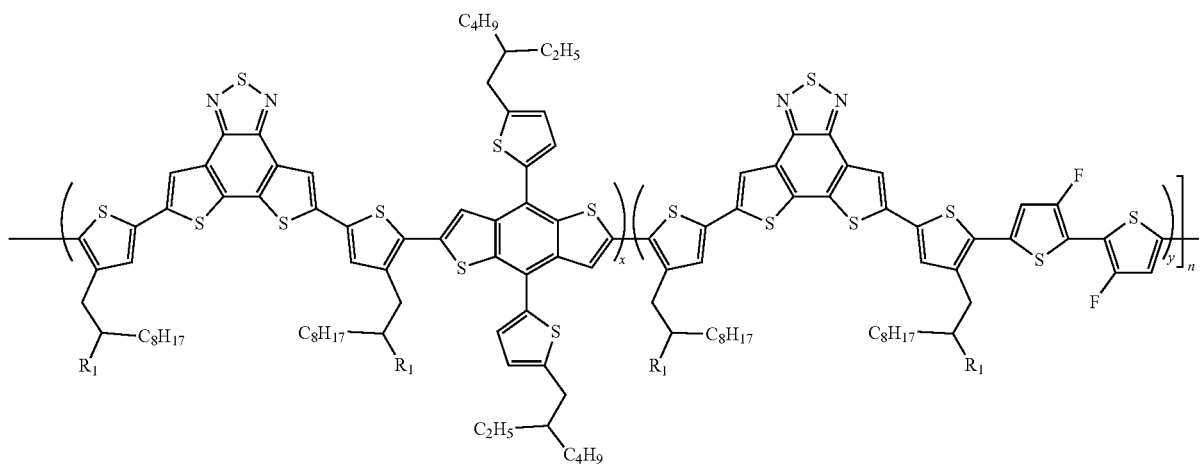

wherein the compositional ratio of x/y ranges from about 1/99 to about 99/1, and n ranges from 1 to 1,000,000. In this composition, $R_1$ is selected from: H, unsubstituted or substituted branched alkyls with 1 to 60 carbon atoms, or unsubstituted or substituted linear alkyls with 1 to 60 carbon atoms.

In other non-limiting embodiments, combinations can be contemplated such as $R_5$ and $R_6$ are H, $R_9$ and $R_{10}$ are F, $R_9$ and $R_{10}$ are H, $R_7$ and $R_8$ are Cl, or even $R_7$ and $R_8$ are F.

In these embodiments, the compositional ratio of x/y ranges from about 1/99 to about 99/1, and n ranges from 1 to 1,000,000.

In other embodiments, the compositional ratio of x/y ranges from about 10/90 to about 90/10, or even from about 30/70 to about 90/10.

In other embodiments, composition can comprise:

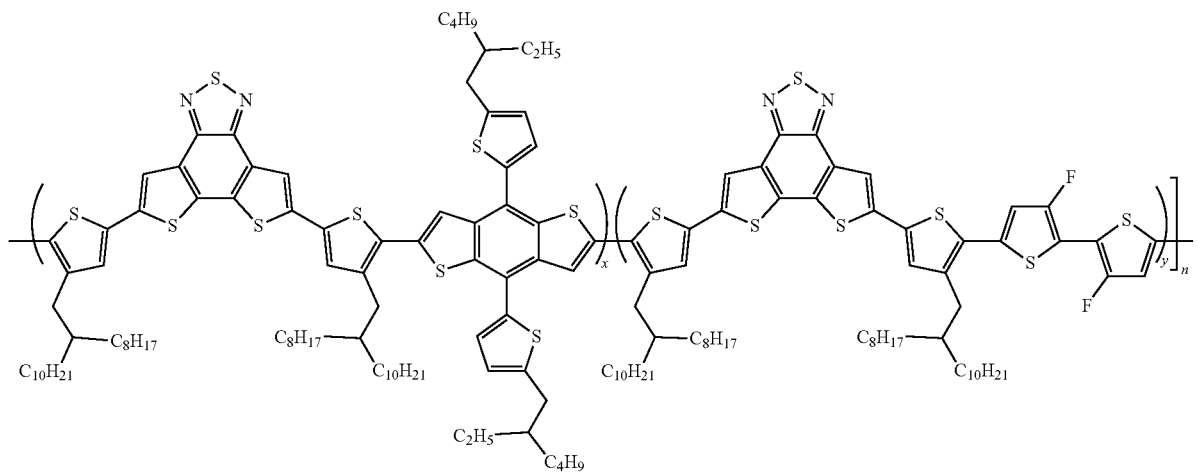

wherein the compositional ratio of x/y can be 50/50, 30/70, 90/10, or even 60/40,

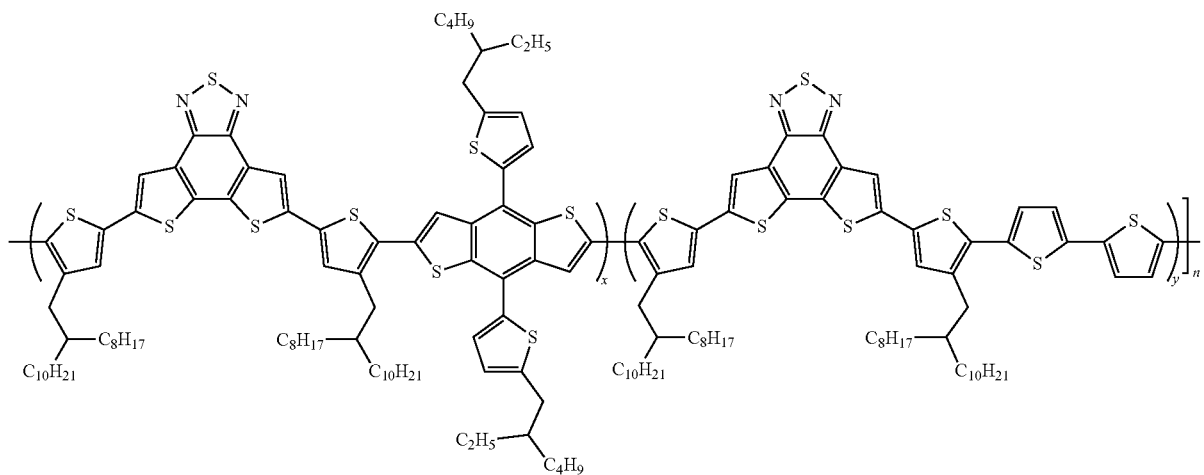

wherein the compositional ratio of x/y can be 50/50,
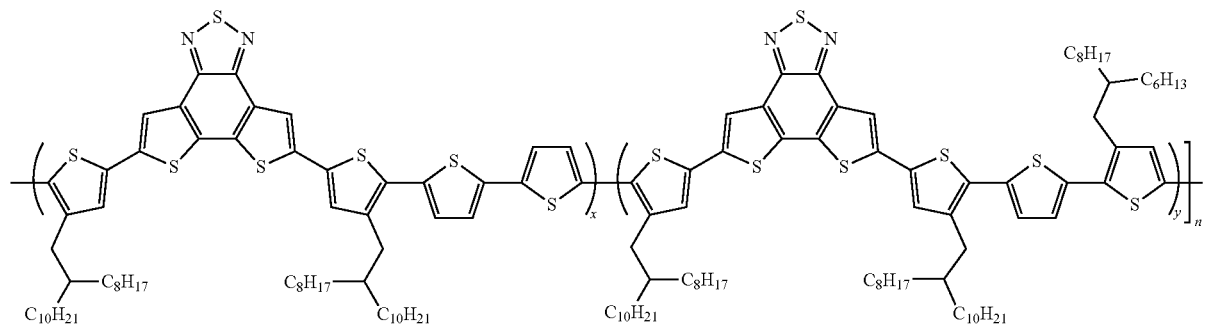
wherein the compositional ratio of x/y can be 80/20,
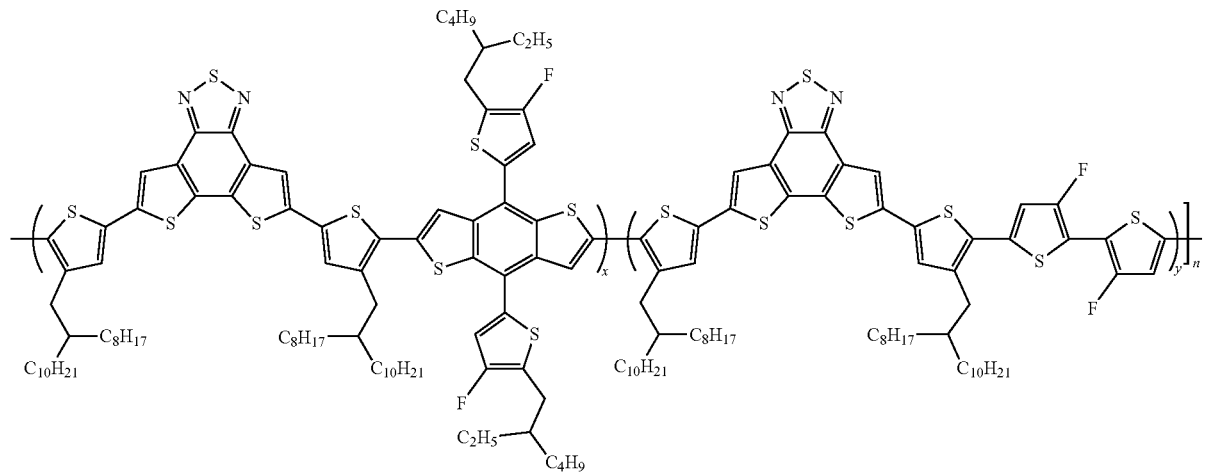
wherein the compositional ratio of x/y is 50/50,
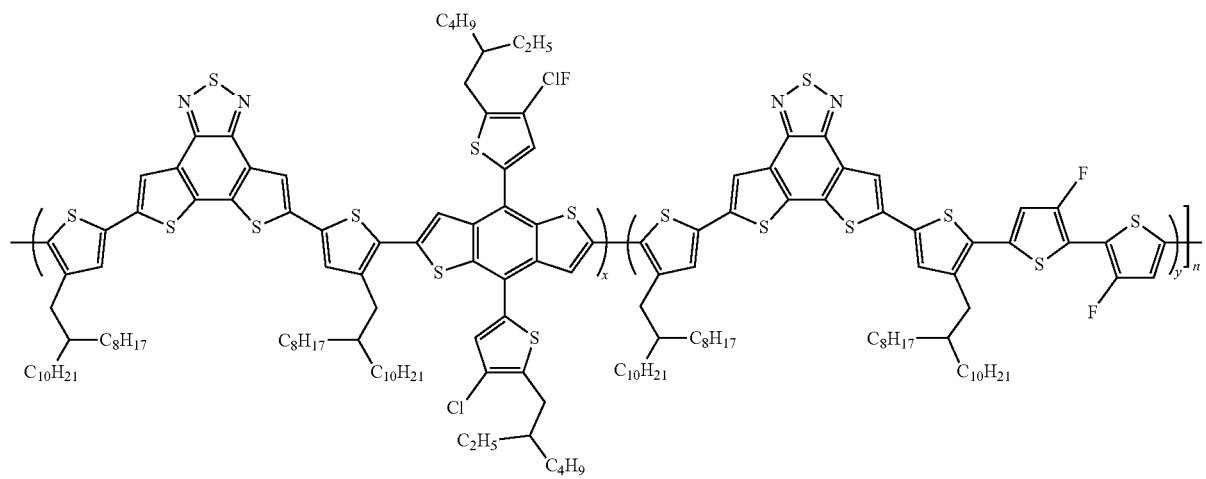

wherein the compositional ratio of x/y is 50/50,

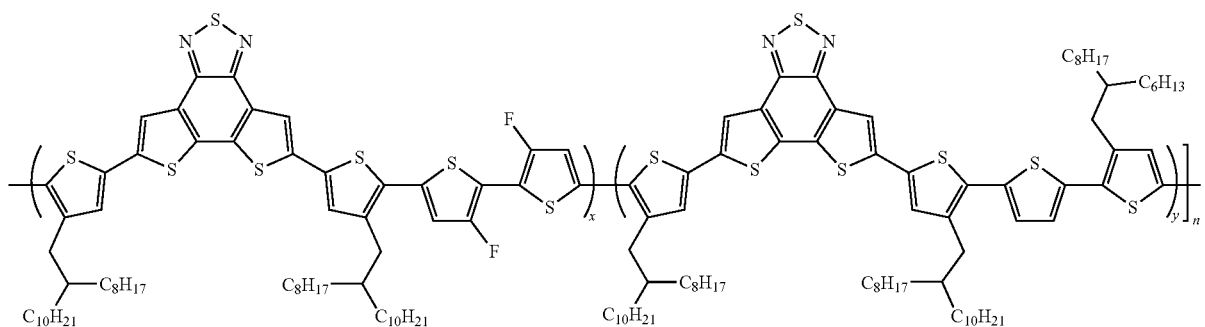

wherein the compositional ratio of x/y is 80/20, or even

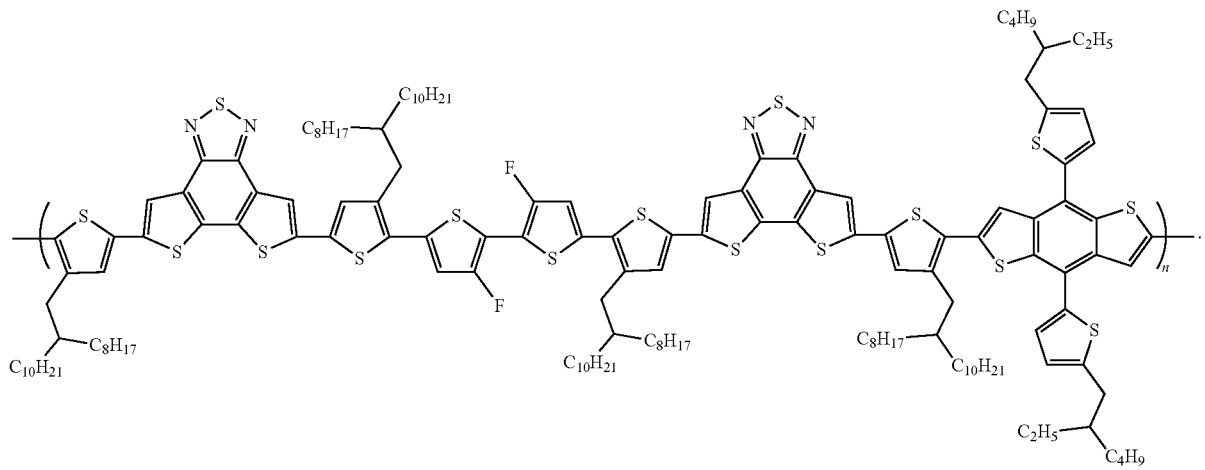

In some embodiments, the composition can be used as a photovoltaic material, an active layer material, a semiconducting material, or even a donor material blended with an acceptor material.

In yet other embodiments, the composition is a random copolymer.

The following examples of certain embodiments of the invention are given. Each example is provided by way of explanation of the invention, one of many embodiments of the invention, and the following examples should not be read to limit, or define, the scope of the invention.

Device Architecture

When used as a photovoltaic device the architecture may be a conventional architecture device, while in others it may be an inverted architecture device. A conventional architecture device typically comprised of multilayered structure with a transparent anode as a substrate to collect positive charge (holes) and a cathode to collect negative charge (electrons), and a photo-active layer sandwiched in between two electrodes. An additional charge transport interlayer is inserted in between active layer and electrode for facile hole and electron transport. Each charge transport layer can be consisted of one or more layers. An inverted device has the same multilayered structure as the conventional architecture device whereas it uses a transparent cathode as a substrate to collect electrons and an anode to collect holes. The inverted device also has the photo-active layer and additional charge transport layers sandwiched in between two electrodes. FIG. 1 depicts a conventional device architecture and an inverted device architecture.

Monomers

A method wherein

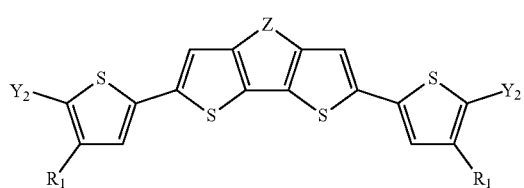

is reacted with

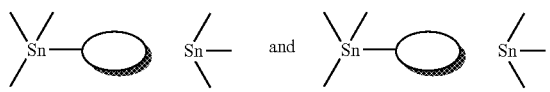

to produce the polymer:

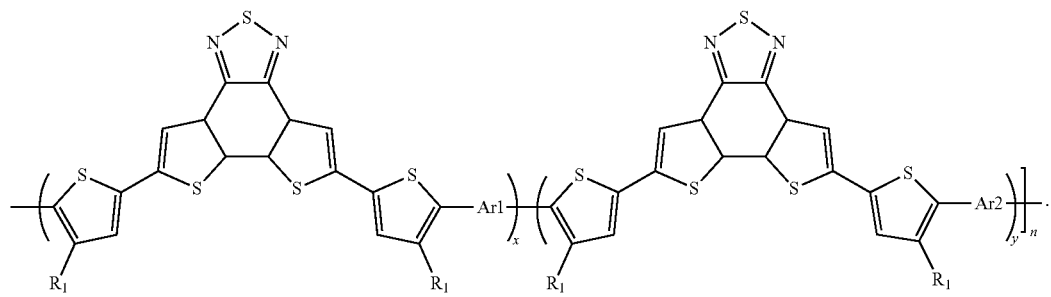

In this method Ar1 is independently selected from the group consisting of:

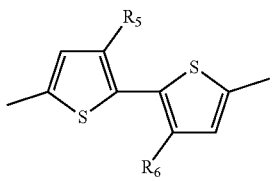

and

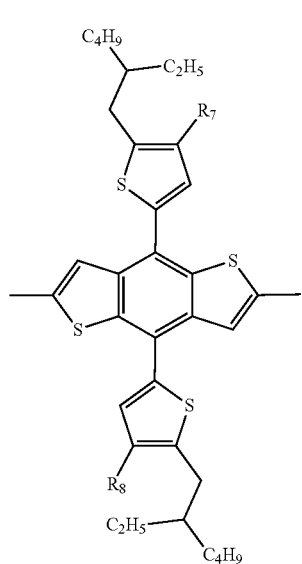

and Ar2 is selected from

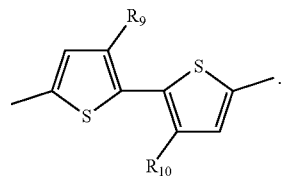

In this method $R_1$, $R_5$, $R_6$, $R_7$, $R_8$, $R_9$, and $R_{10}$ are independently selected from F, Cl, H, unsubstituted or substituted branched alkyls with 1 to 60 carbon atoms, and unsubstituted or substituted linear alkyls with 1 to 60 carbon atoms; wherein Z is a divalent linking group selected from the group consisting of

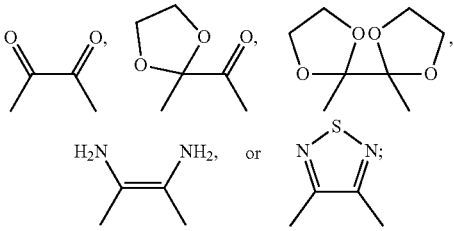

and wherein the compositional ratio of x/y ranges from about 1/99 to about 99/1, and n ranges from 1 to 1,000,000.

In an alternate embodiment, a method is taught wherein

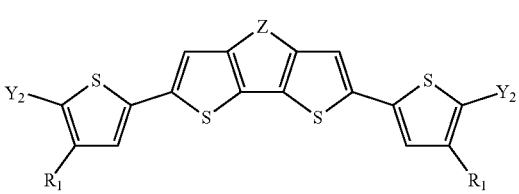

is reacted with 1,1'-(3,3'-difluoro[2,2'-bithiophene]-5,5'-diyl)bis[1,1,1-trimethylstannane] and 4,8-bis[5-(2-ethylhexyl)thien-2-yl]-2,6-bis(trimethylstannyl)benzo[1,2-b']dithiophene to produce the polymer:

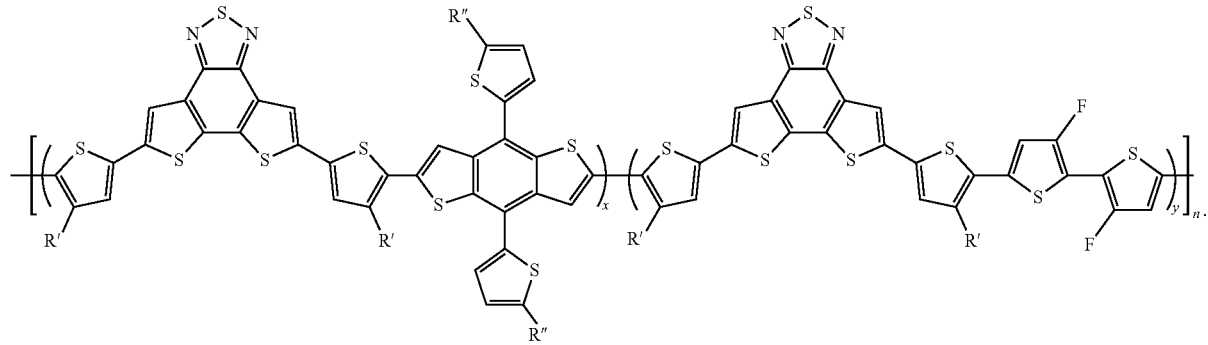

In this polymer the compositional ratio of x/y ranges from about 1/99 to about 99/1, and n ranges from 1 to 1,000,000 and R' and R" are independently selected from: H, unsubstituted or substituted branched alkyls with 1 to 60 carbon atoms, or unsubstituted or substituted linear alkyls with 1 to 60 carbon atoms. Furthermore, in this method $R_1$ is selected from F, Cl, H, unsubstituted or substituted branched alkyls with 1 to 60 carbon atoms, and unsubstituted or substituted linear alkyls with 1 to 60 carbon atoms. Additionally, in this method, $Y_2$ is independently selected from Cl, Br, or I.

A method of reacting

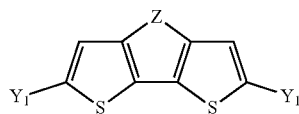

with

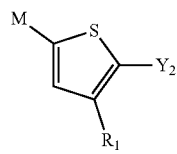

to produce

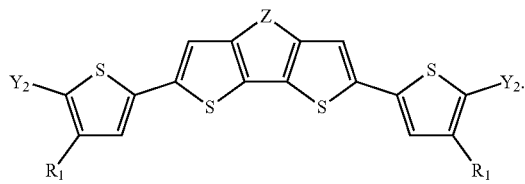

In this method $Y_1$ and $Y_2$ are independently selected from the group consisting of: H, Cl, Br, I, and combinations thereof. Additionally in this method M is selected from the group consisting of H, trialkylstannane, boronate, or ZnX, wherein X is Cl, Br, or I. Furthermore in this method Z is a divalent linking group selected from the group consisting of:

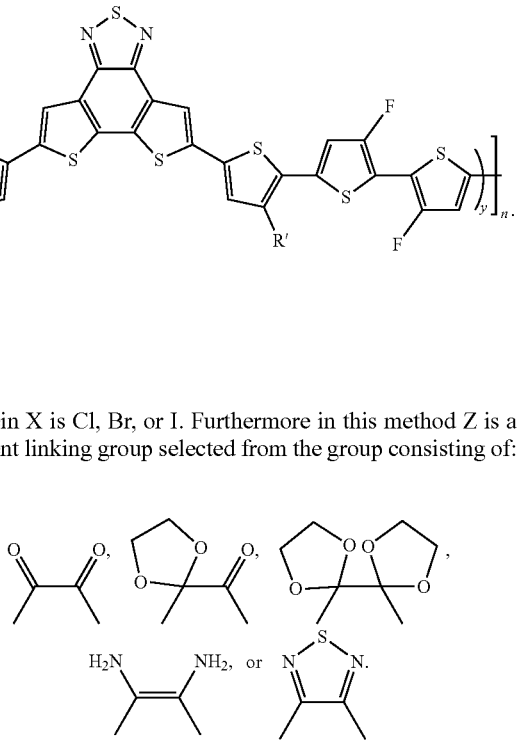

Lastly, in this method $R_1$ is selected from: H, unsubstituted or substituted branched alkyls with 1 to 60 carbon atoms or unsubstituted or substituted linear alkyls with 1 to 60 carbon atoms.

In this method

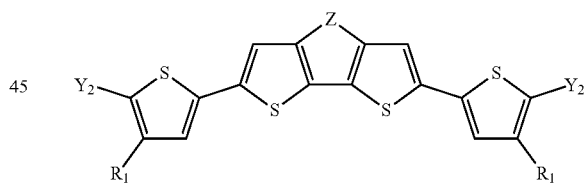

can be further reacted to produce

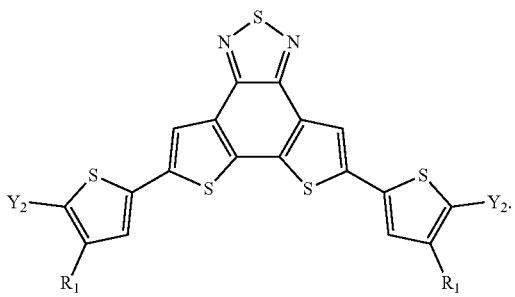

Alternatively, $R_1$ can be selected from 2-hexyldecyl or 2-octyldodecyl alkane. In other embodiments, when $Y_1$ is H, $Y_2$ is Cl, Br, I. Or when $Y_2$ is H, $Y_1$ is Cl, Br, I. Furthermore, an embodiment can exist where M or $Y_2$ is H. Such features can include when M is H, $Y_2$ is Cl, Br, I. Or when $Y_2$ is H, M is trialkylstannane, boronate, or ZnX, wherein X is Cl, Br, or I.
In some embodiments of the method,
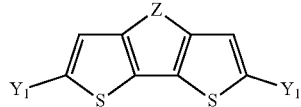
is
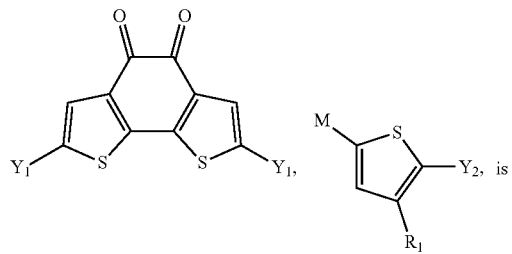
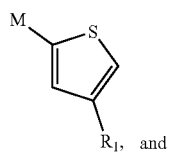
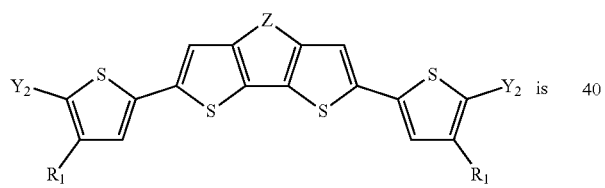
In other embodiments of the method,
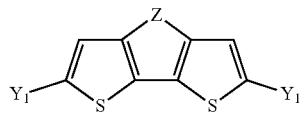
is
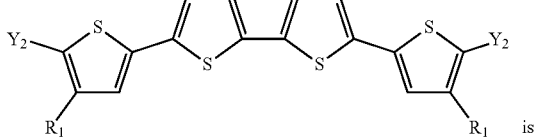
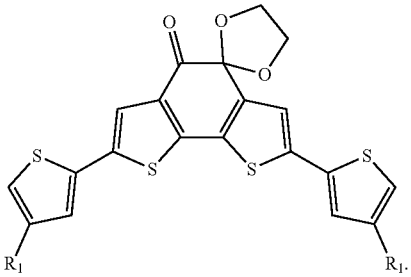
In yet further embodiments of the method,
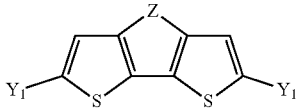
is
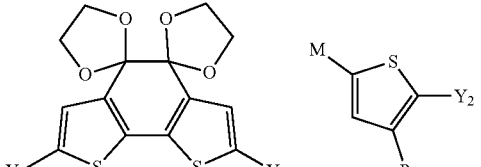
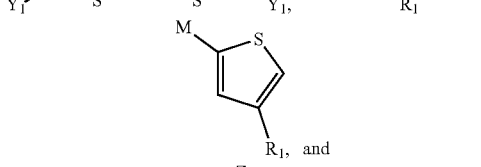
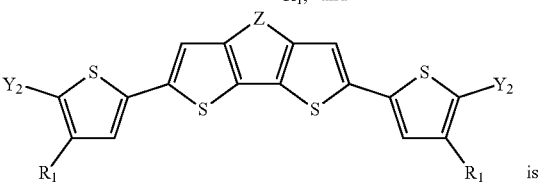
is -continued
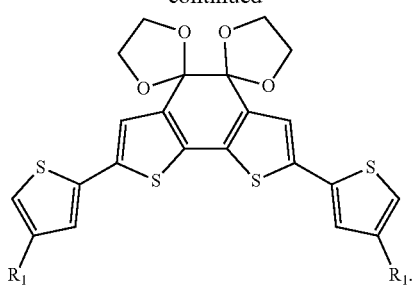
In yet another embodiment of the method,
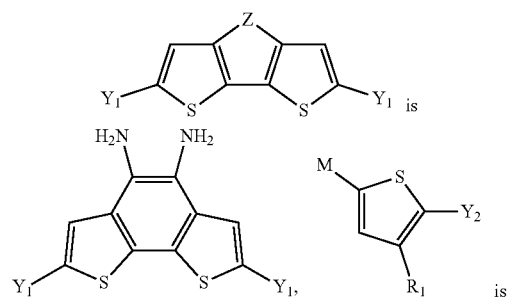
In other embodiments,
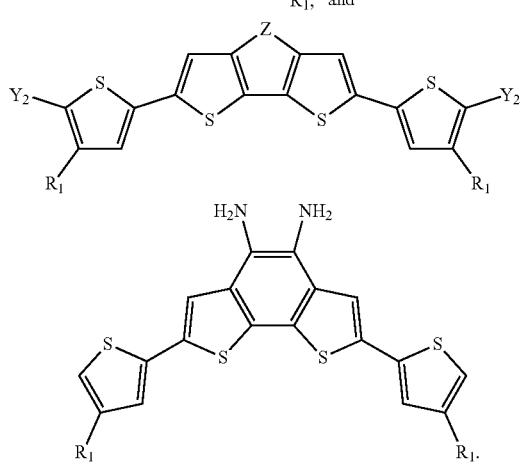
can be further reacted to produce
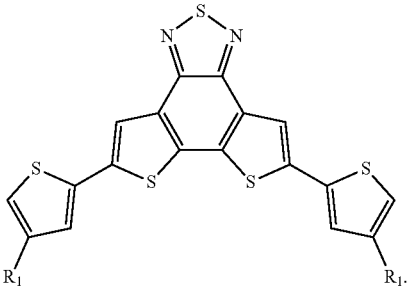
In other methods,
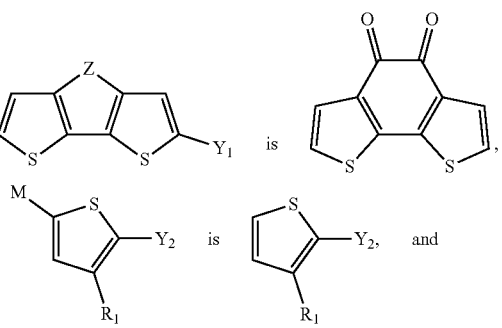
In yet more embodiments of the method,
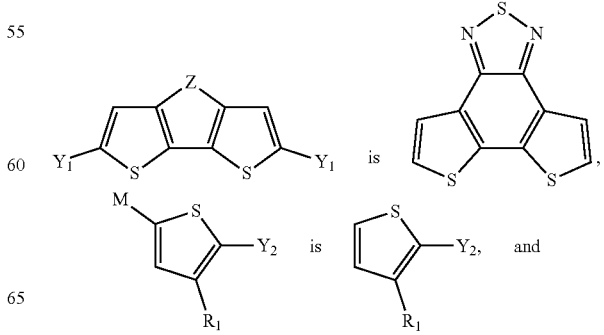

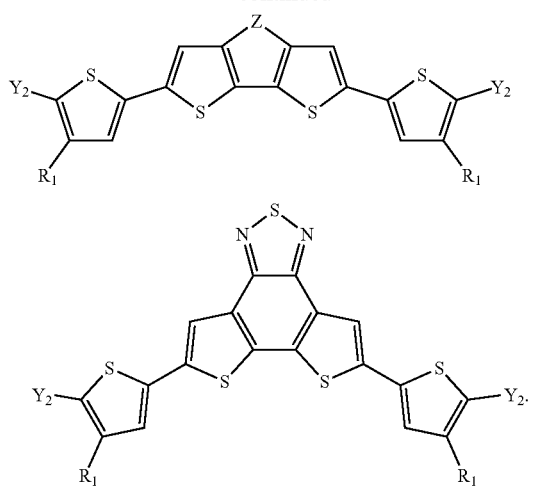
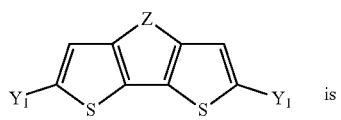
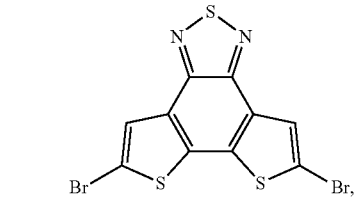
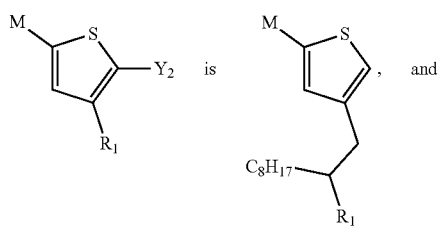
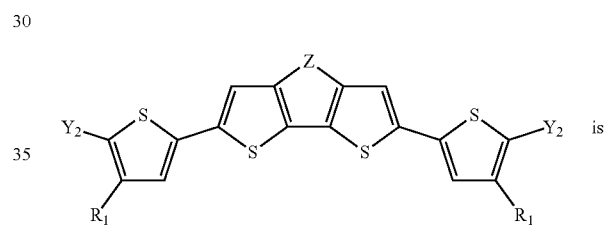
In yet further embodiments of the method,
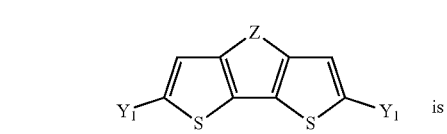
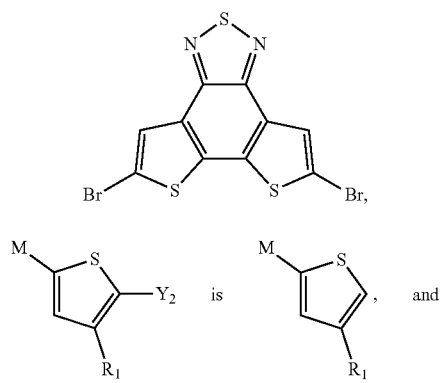
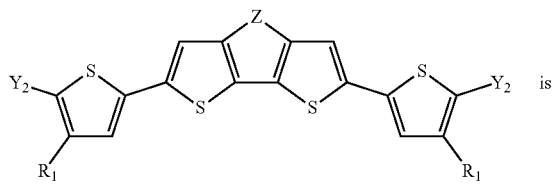
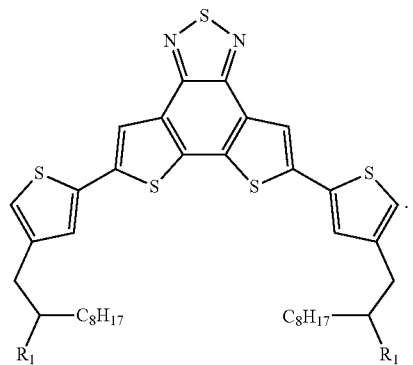
In even more embodiments of the method,
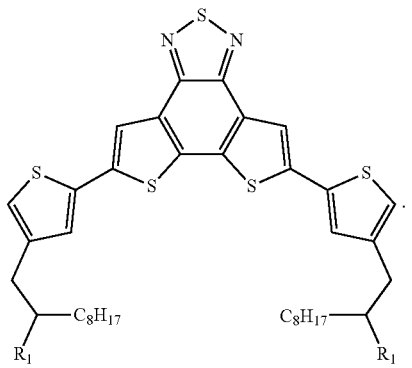
In some embodiments of the method, is
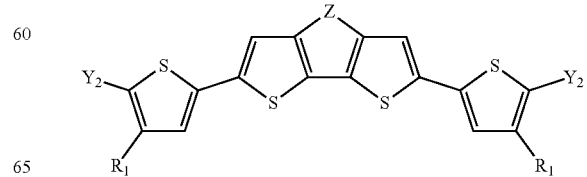

further reacted to produce
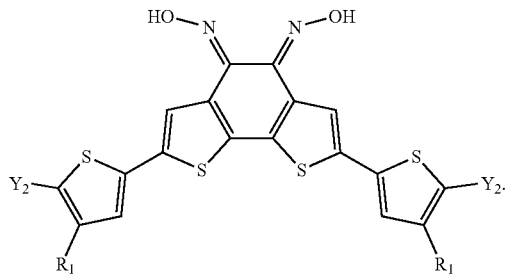
In this embodiment,
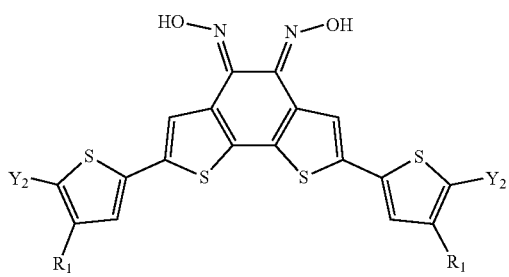
is further reacted to produce
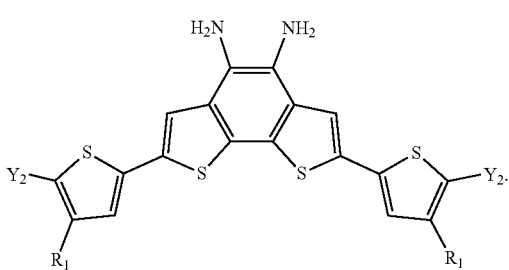
Eventually,
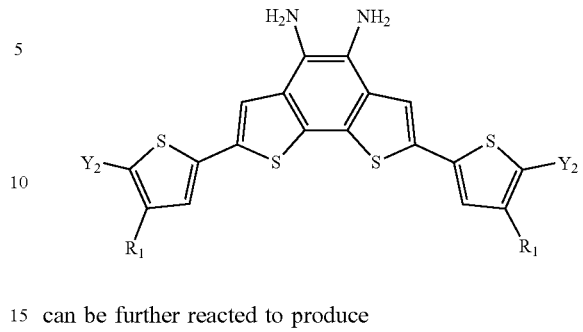
can be further reacted to produce
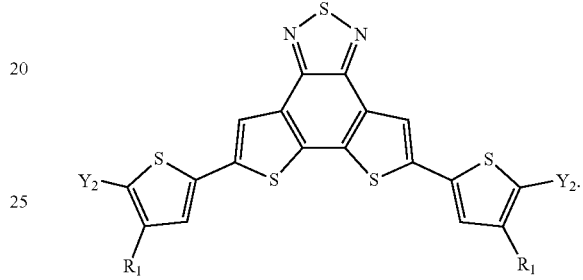
In some embodiments,
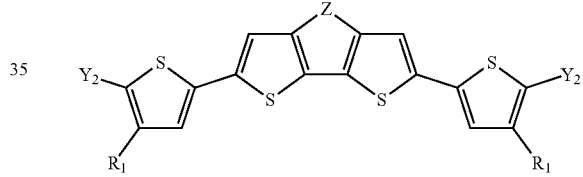
is reacted with
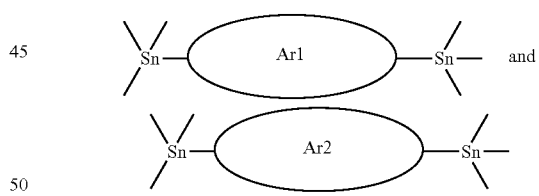
to produce the polymer:
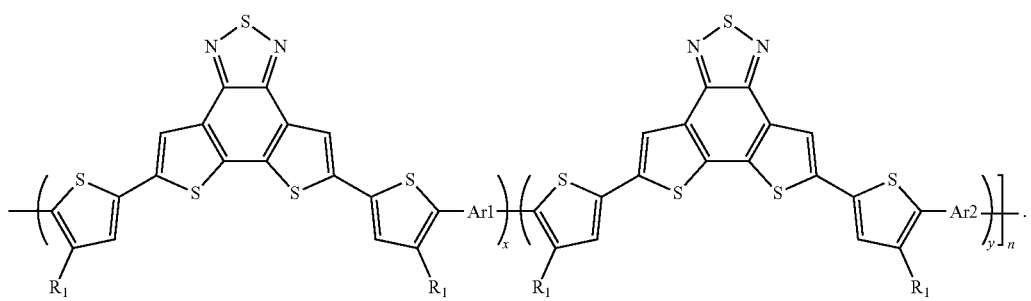

In this embodiment, Ar1 is independently selected from the group consisting of:

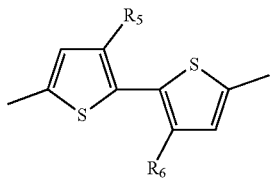

and

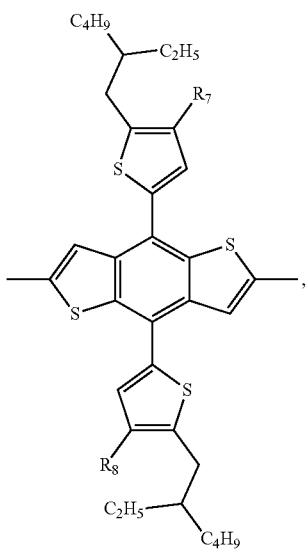

and Ar2 can be selected from

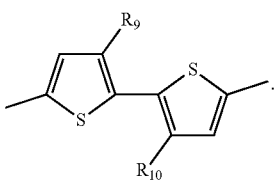

Furthermore R$_1$, R$_5$, R$_6$, R$_7$, R$_8$, R$_9$, and R$_{10}$ are independently selected from F, Cl, H, unsubstituted or substituted branched alkyls with 1 to 60 carbon atoms, and unsubstituted or substituted linear alkyls with 1 to 60 carbon atoms.

In some embodiments, the method does not produce

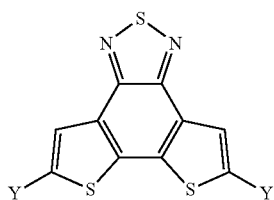

wherein Y is selected from the group consisting of Cl, Br, and I. In other embodiments, R1 is selected from 2-hexyldecyl or 2-octyldodecyl.alkane.

Figure 2:
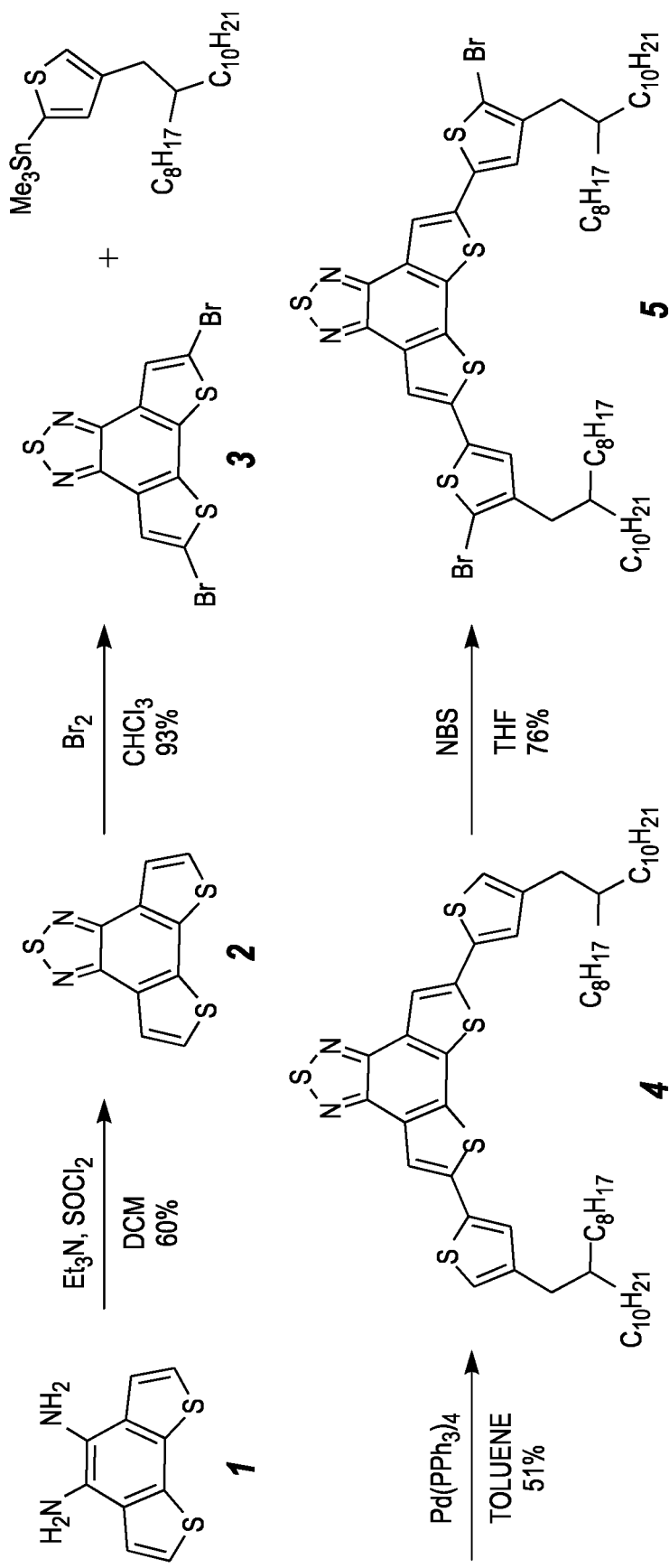
FIG. 2 depicts a method of making a monomer.

FIG. 2 depicts a method of preparing the following monomer

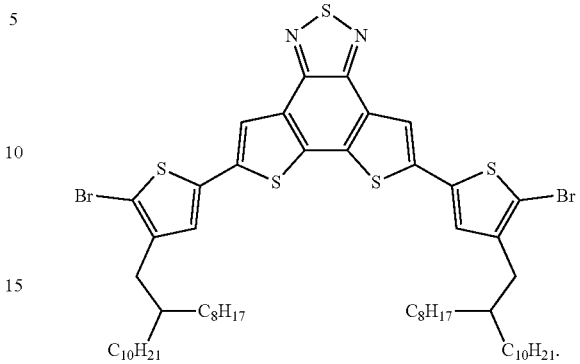

As shown in FIG. 2, compound 2 was prepared by taking compound 1 and adding dry methylene chloride and triethylamine. Thionyl chloride is then added and the mixture is heated. The reaction is then cooled and extracted with dichloromethane. The organic layer was dried, filtered, and concentrated. Pure fractions were concentrated to afford compound 2 (10.3 mmol, 60% yield) as a tan solid.

Compound 3 of FIG. 2 is then prepared by taking compound 2 and adding dry chloroform and bromine. The reaction is then heated and then cooled. The solid was dried under vacuum to afford the product, compound 3 (1.8 mmol, 93% yield).

Compound 4 of FIG. 2 is then prepared by taking compound 3 and combining it with 2-(trimethylstannyl)-4-(2-octyldodecyl))thiophene. The reaction is then heated and reacted with tetrakis(triphenylphosphine)palladium(0). The reaction was then cooled, and the residue was dissolved in dichloromethane to obtain the desired product, compound 4 (1.2 mmol, 51% yield).

Compound 5 of FIG. 2 is then prepared by taking reacting compound 4 in tetrahydrofuran and treated with a solution of N-bromosuccinimide in THF. The product, compound 5 (1.1 mmol, 76% yield), was an orange solid.

Compound 7,

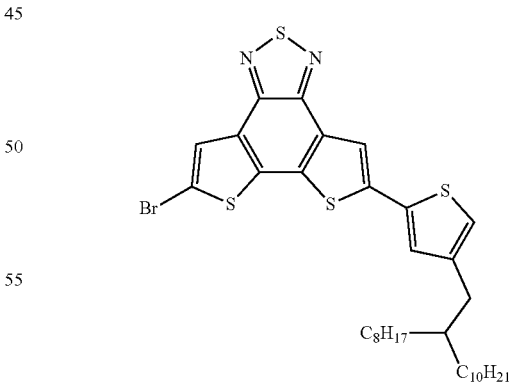

is then prepared by reacting compound 3 and dry toluene. The mixture is then mixed with tetrakis(triphenylphosphine) palladium(0) and 2-(trimethylstannyl)-4-(2-octyldodecyl)) thiophene. The reaction continues till the crude material is diluted with a mixture of dichloromethane and chloroform. This mixture is then filtered to afford compound 7 (0.83 mmol, 34% yield).

Compound 8,

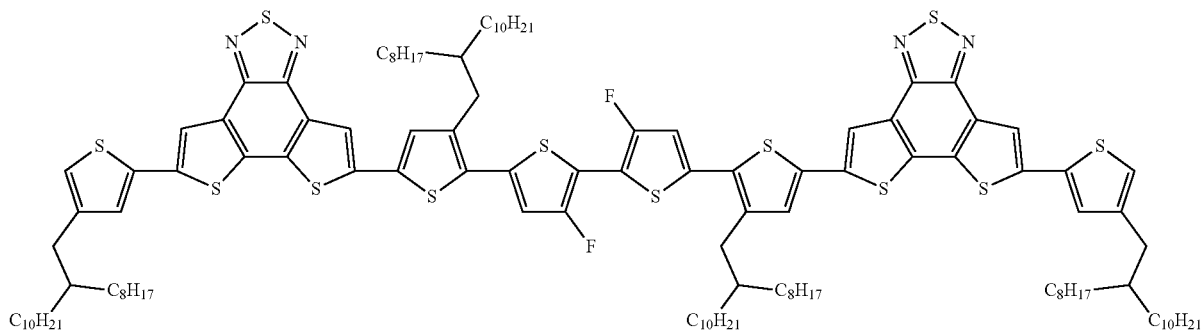

is then prepared by reacting compound 7 and stannane, 1,1'-[3",4'-difluoro-3,3'''-bis(2-octyldodecyl)[2,2':5',2":5", 2'''-quaterthiophene]-5,5'''-diyl]bis[1,1,1-trimethyl. The reaction was then heated and tetrakis(triphenylphosphine)palladium(0) was added to produce compound 8 (0.091 mmol, 56% yield) as a red-violet solid.

Compound 9,

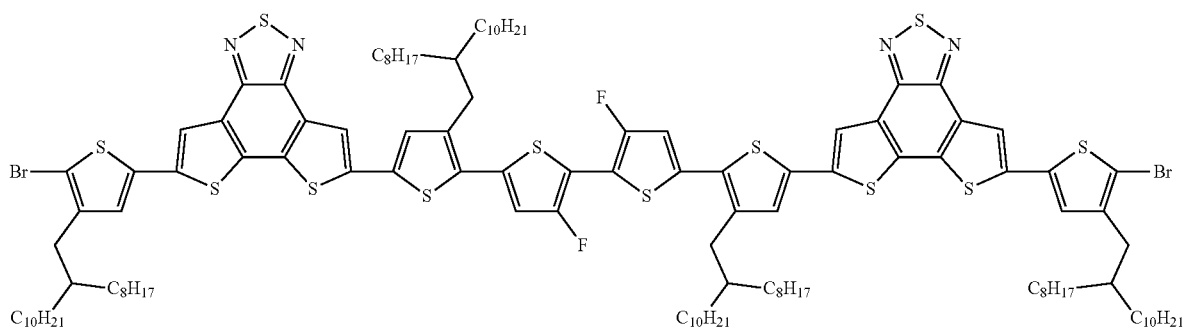

is produced by taking compound 8 and adding tetrahydrofuran and N-bromosuccinimide. This mixture produces compound 9 (0.011 mmol, 93% yield) as a red-violet solid.

In alternate embodiments, compound 5 can be created from different reaction mechanisms. In all these reaction schemes

Figure 3:
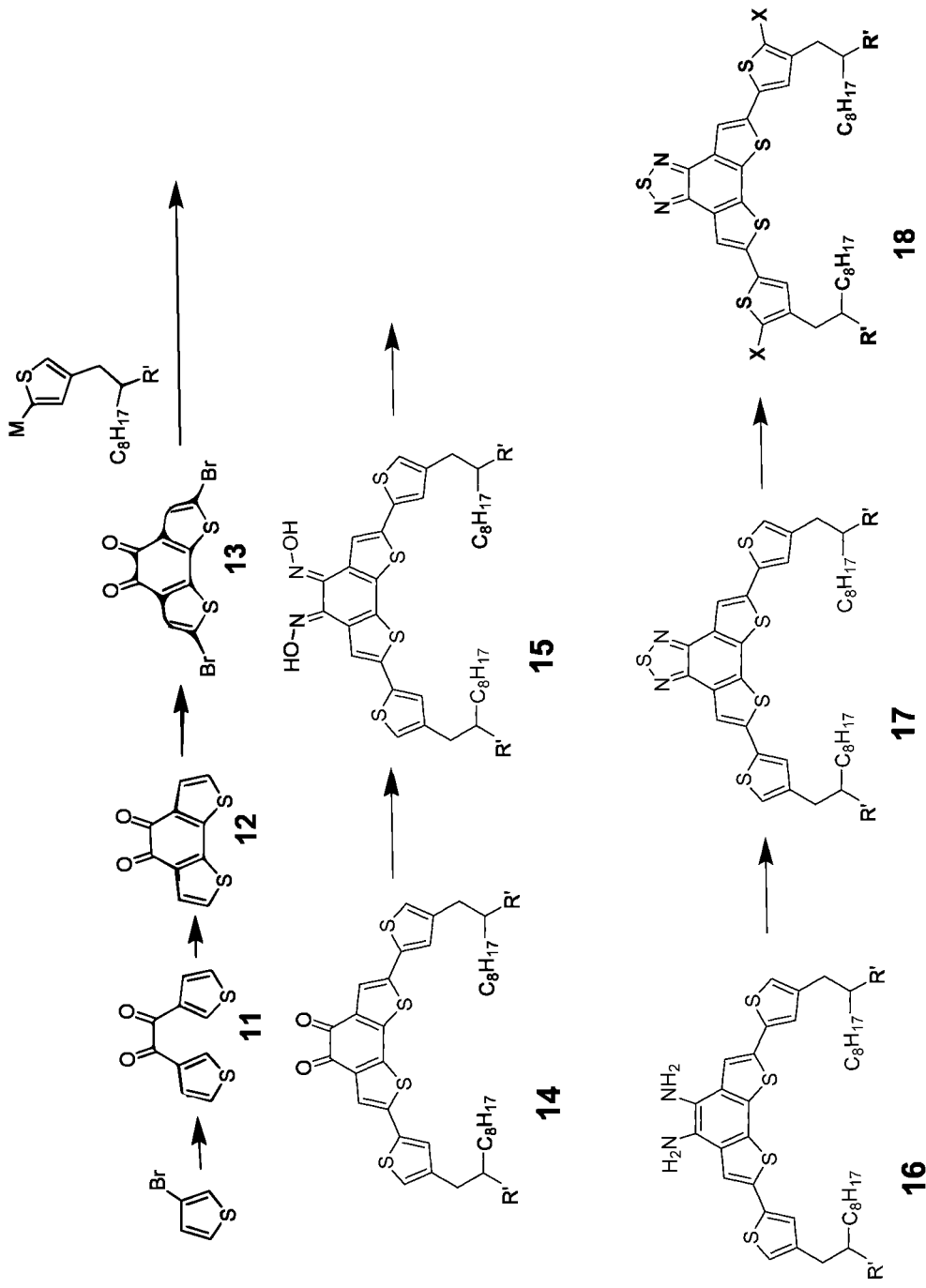
FIG. 3 depicts a method of making a monomer.

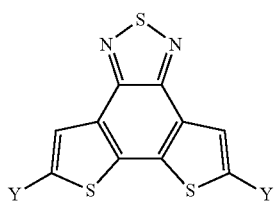

is not produced, where Y is Cl, Br, or I. As shown in FIG. 3, compound 5 herein labelled as compound 18 can be created from shown reaction scheme. In this reaction scheme, X is independently selected from: H, Cl, or Br. R' can selected from: unsubstituted or substituted branched alkyls with 1 to 60 carbon atoms, unsubstituted or substituted linear alkyls with 1 to 60 carbon atoms, $C_6H_{13}$, or $C_{10}H_{21}$. Furthermore, in this reaction scheme, M is selected from: trialkylstannane, boronate, or ZnX, wherein the X of ZnX is selected from Cl, Br, or I. The individual reactions between the compounds can be any conventionally known reaction known to one skilled in the art.

As a non-limiting embodiment of FIG. 3, 1,2-di(thiophen-3-yl)ethane-1,2-dione can be added to anhydrous $FeCl_3$ and anhydrous dichloromethane to produce compound 12. Compound 12 can then be brominated with N-bromosuccinimide to produce compound 13. Tris(dibenzylideneacetone)dipalladium(0) and tri(o-tolyl)phosphine can then be added to compound 13 to produce compound 14. Hydroxylamine hydrochloride can then be added to compound 14 to produce compound 15. Hydrazine monohydrate can then be added to compound 15 to produce compound 16. Thionyl chloride can then be added to compound 16 to produce compound 17. Compound 17 can then be halogenated to produce compound 18.

As shown in FIG. 3, compound benzo[2,1-b:3,4-b']dithiophene-4,5-dione (1.91 g, 8.7 mmol) was added into a flask and then vacuumed and backed filled with argon 3 times. Anhydrous dimethylformamide and N-bromosuccinimide were added. A solid (3.0 g, yield 91.5%) of product 13 were obtained.

In a flask, compound 2,7-dibromobenzo[2,1-b:3,4-b']dithiophene-4,5-dione (1 g, 2.65 mmol), tris(dibenzylideneacetone)dipalladium(0) (48.0 mg, 0.053 mmol), and tri(o-tolyl)phosphine (64.0 mg, 0.212 mmol) were combined. The crude material was dissolved in dichloromethane, adsorbed onto silica gel, and purified. Product 2,7-bis(4-(2-hexyldecyl)thiophen-2-yl)benzo[2,1-b:3,4-b']dithiophene-4,5-dione (300 mg, yield 13.6%) was obtained after the removal of solvent. A side product of 2-bromo-7-(4-(2-hexyldecyl)thiophen-2-yl)benzo[2,1-b:3,4-b']dithiophene-4,5-dione was also obtained.

Compound 2,7-bis(4-(2-hexyldecyl)thiophen-2-yl)benzo[2,1-b:3,4-b']dithiophene-4,5-dione (0.3 g, 0.36 mmol) and hydroxylamine hydrochloride (0.2 g, 2.878 mmol) were added into a flask. Analysis showed product 15 was obtained.

The previous product 15 solution (0.3 g, 0.36 mmol) was added 20 mg Pd/C (10%, 0.06 mmol). and hydrazine monohydrate (500 mg, 10 mmol) and dry ethanol was added dropwise. Analysis results confirmed product 16 were obtained.

The previous 16 crude (0.36 mmol) was vacuumed and backfilled with argon three times before triethylamine (1.0 g, 9.8 mmol) was added. After the reaction was cooled down to room temperature, analysis results confirmed product 17 were obtained.

The previous 17 crude (0.36 mmol) with excess of thionyl chloride in DCM solvent. Product 18 (120 mg, yield 35.8%) was obtained after the removal of solvent.

A solution of compound 17 (1.47 g, 1.5 mmol) in tetrahydrofuran (15 mL) was cooled to 0° C. and treated slowly with a solution of N-bromosuccinimide (0.645 g, 3.6 mmol) in THF. The product, compound 18 (1.3 g, 1.1 mmol, 76% yield), was obtained as a solid.

Figure 4:
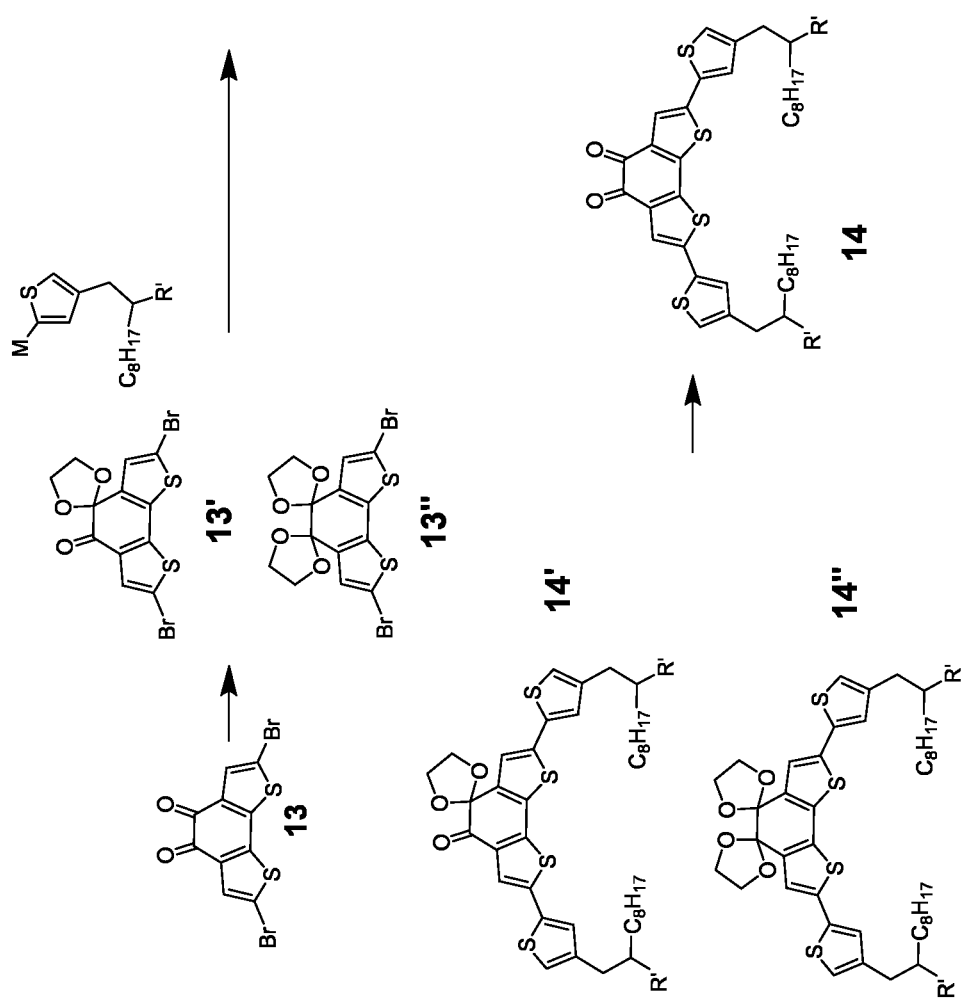
FIG. 4 depicts an optional protection step when making a monomer.

FIG. 4 demonstrates a protection scheme that can be used with the reaction scheme shown in FIG. 3, or FIGS. 5-8 below to prevent the formation of

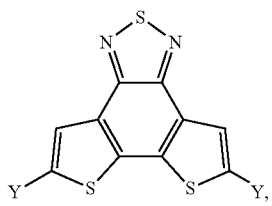

wherein Y is a halogen.

Compound 2,7-dibromobenzo[2,1-b:3,4-b']dithiophene-4,5-dione 13 (2.5 g, 6.6 mmol) was reacted with ethylene glycol (10 mL) and toluene (200 mL). Powder of mixture of 13" and 13' (2.9 g, yield of 94%) was obtained.

In a flask, a mixture of compounds 2,7-dibromo-5H-spiro[benzo[2,1-b:3,4-b']dithiophene-4,2'-[1,3]dioxolan]-5-one and 13' and 2',7'-dibromodispiro[[1,3]dioxolane-2,4'-benzo[2,1-b:3,4-b']dithiophene-5',2"-[1,3]dioxolane] 13" (1.1 g, 2.61 mmol), and tetrakis(triphenylphosphine)palladium(0) (150 mg, 0.13 mmol) were combined. Analysis showed mixture of product 14' and 14".

In a flask, compound 2,7-bis(4-(2-octyldodecyl)thiophen-2-yl)-5H-spiro[benzo[2,1-b:3,4-b']dithiophene-4,2'-[1,3]dioxolan]-5-one 14' (1.0 g) from previous reaction was added with acetic acid and hydrochloric acid. Analysis showed formation of product of 14.

Figure 5:
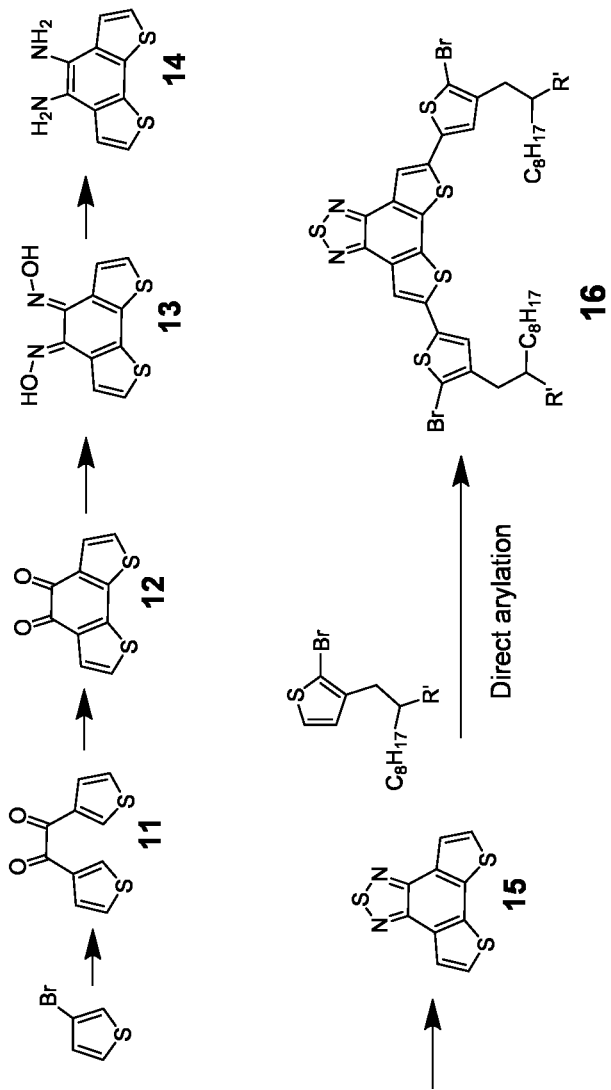
FIG. 5 depicts a method of making a monomer.

FIG. 5 shows another reaction scheme to produce compound 5 herein labelled as compound 16. In this reaction scheme, the coupling reaction can be direct arylation to produce 16. Lastly in this reaction scheme

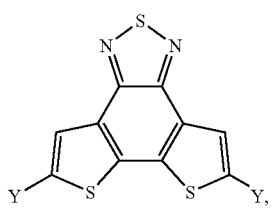

where Y is a halogen, is not produced.

Figure 6:
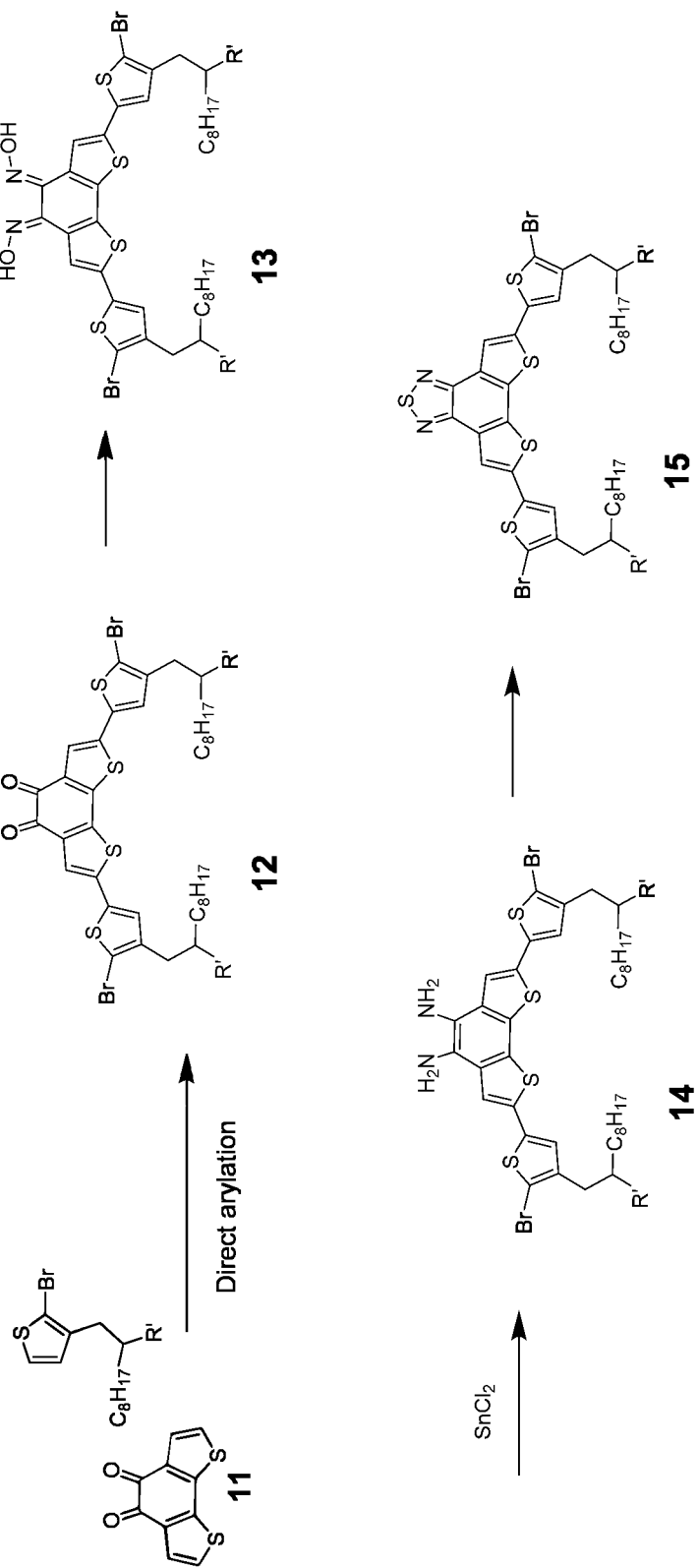
FIG. 6 depicts a method of making a monomer.

FIG. 6 shows another reaction scheme to produce compound 5 herein labelled as compound 15. In this reaction scheme, a coupling reaction can be done through direct arylation to produce 12, which is subsequently reacted through methods described in this application to produce 15. An optional SnCl$_2$ reduction step can be done to produce the amine intermediate while not breaking C—X bonds.

To a round bottom flask under the flow of argon compound

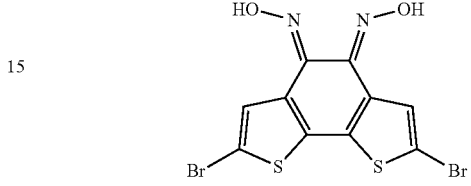

(0.75 g, 1.84 mmol) was added to 200-proof ethanol. A solution of SnCl$_2$ in HCl (10 mL, 10.4 mmol) was added dropwise. The desired product

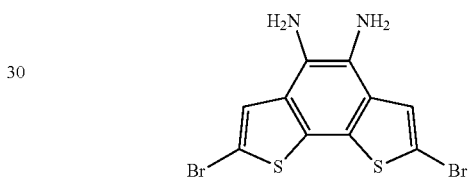

was obtained as a red solid after the removal of the solution.

Figure 7:
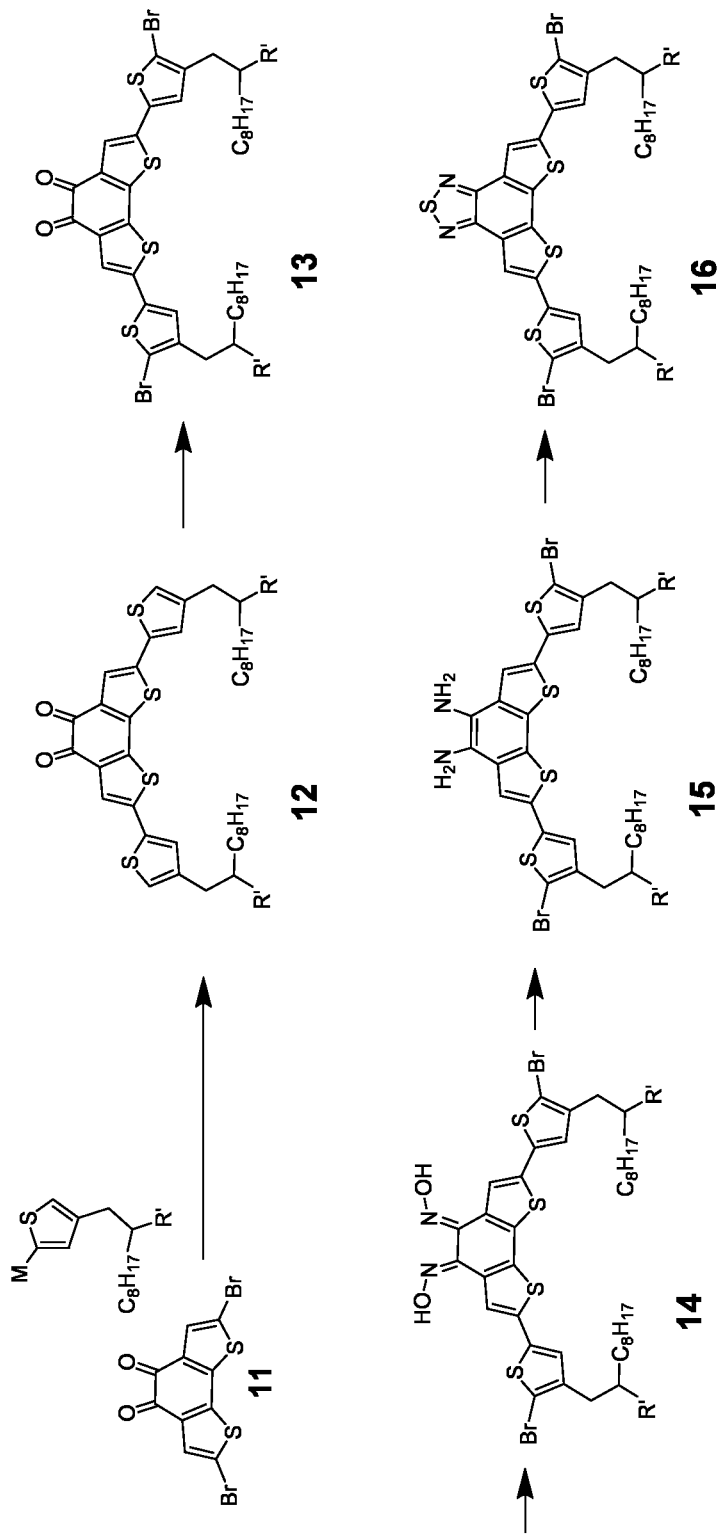
FIG. 7 depicts a method of making a monomer.

FIG. 7 shows another reaction scheme to produce compound 5 herein labelled as compound 16. The individual reactions between the compounds are described elsewhere and can be any conventionally known reaction known to one skilled in the art. Lastly in this reaction scheme

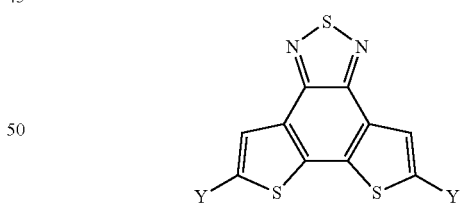

is not produced, wherein Y is a halogen.

Figure 8:
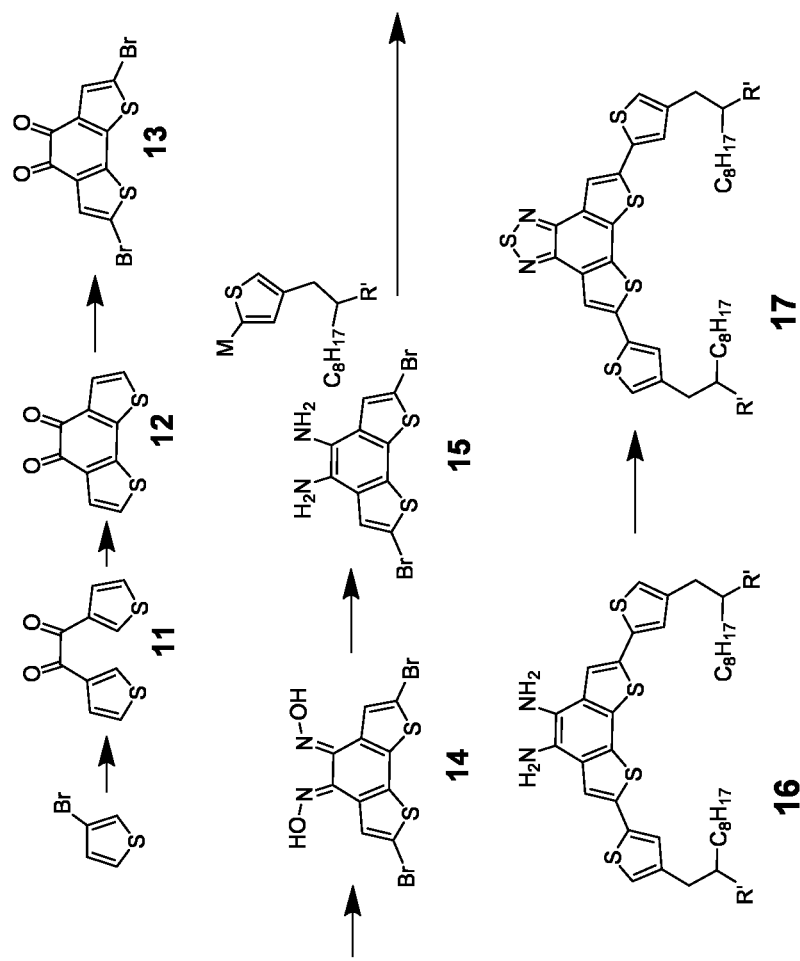
FIG. 8 depicts a method of making a monomer.

FIG. 8 shows another reaction scheme to produce compound 5 herein labelled as compound 17. R' can selected from: unsubstituted or substituted branched alkyls with 1 to 60 carbon atoms, unsubstituted or substituted linear alkyls with 1 to 60 carbon atoms, C$_6$H$_{13}$, or C$_{10}$H$_{21}$. Furthermore, in this reaction scheme, M is selected from: trialkylstannane, boronate, or ZnX, wherein the X of ZnX is selected from Cl, Br, or I. The individual reactions between the compounds can be any conventionally known reaction known to one skilled in the art. Lastly in this reaction scheme

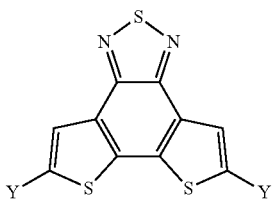

is not produced, wherein Y is a halogen.

Polymer

Polymer A

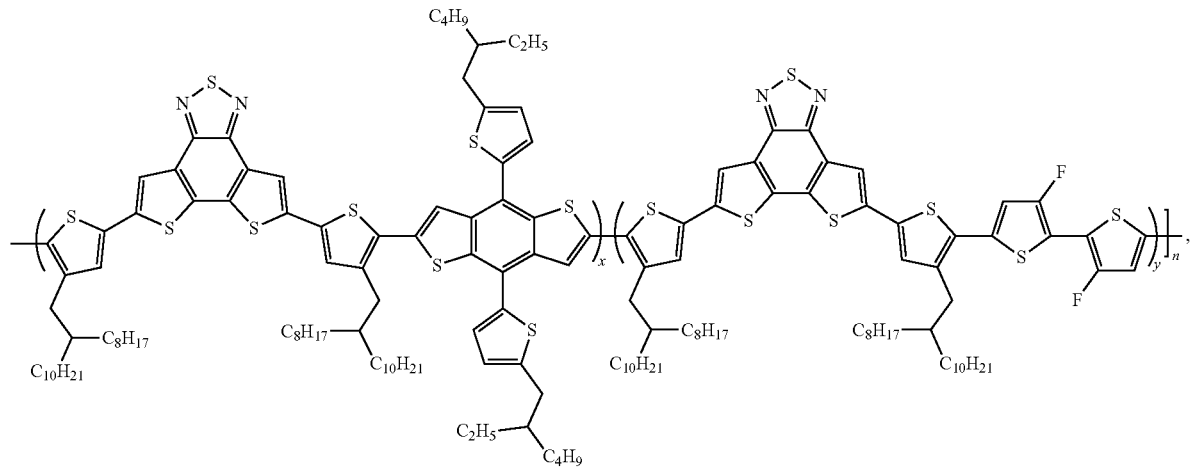

wherein x/y=50/50 is produced by combining compound 5 (0.13 mmol), 1,1'-(3,3'-Difluoro[2,2'-bithiophene]-5,5'-diyl)bis[1,1,1-trimethylstannane] (0.066 mmol), 4,8-Bis[5-(2-ethylhexyl)thien-2-yl]-2,6-bis(trimethylstannyl)benzo[1,2-b:4,5-b']dithiophene (0.066 mmol), tris(dibenzylideneacetone)dipalladium(0) (0.005 mmol), and tri(o-tolyl)phosphine (0.021 mmol). The reaction is heated, then cooled, then finally precipitated with methanol. Polymer A (0.13 mmol, 94% yield) was then collected.

Polymer B

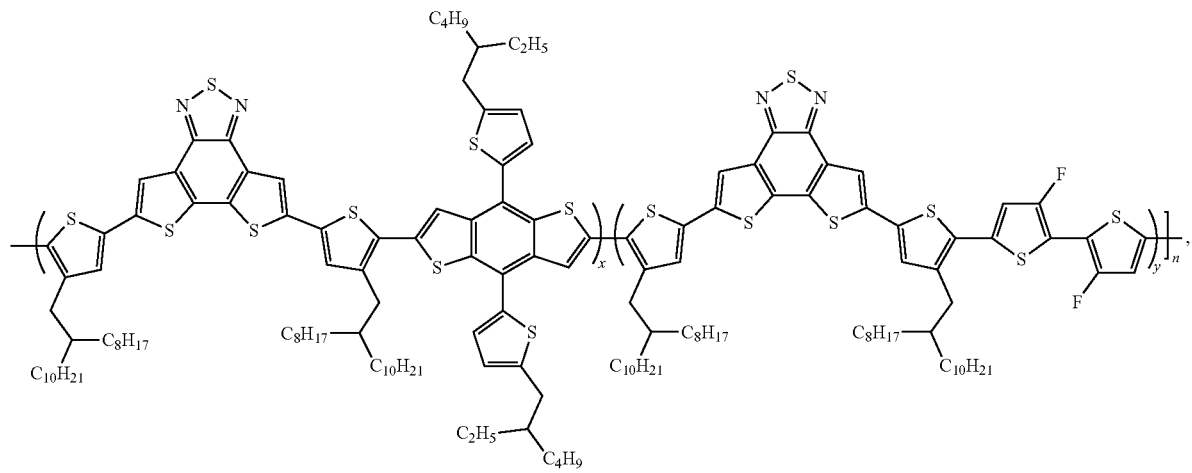

wherein x/y=30/70 is produced by combining 5 (0.14 mmol), 1,1'-(3,3'-Difluoro[2,2'-bithiophene]-5,5'-diyl)bis[1,1,1-trimethylstannane] (0.099 mmol), 4,8-Bis[5-(2-ethylhexyl)thien-2-yl]-2,6-bis(trimethylstannyl)benzo[1,2-b:4,5-b']dithiophene (0.042 mmol), tris(dibenzylideneacetone)dipalladium(0) (0.006 mmol), and tri(o-tolyl)phosphine (0.023 mmol). The reaction is heated, then cooled, then finally precipitated with methanol. Polymer B (0.13 mmol, 91% yield) was then collected.

Polymer C

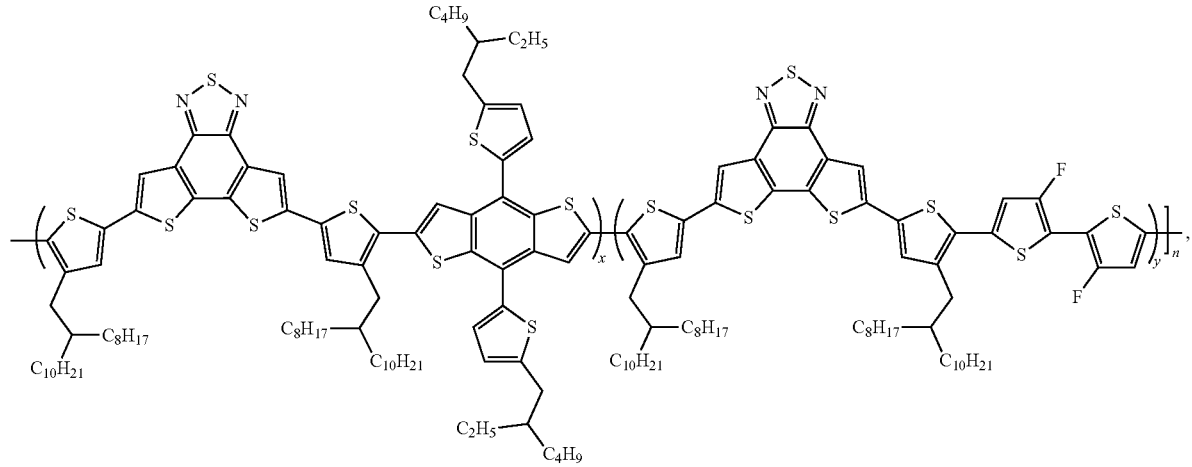

wherein x/y=90/10 is produced by combining compound 5 (0.12 mmol), 1,1'-(3,3'-Difluoro[2,2'-bithiophene]-5,5'-diyl)bis[1,1,1-trimethylstannane] (0.012 mmol), 4,8-Bis[5-(2-ethylhexyl)thien-2-yl]-2,6-bis(trimethylstannyl)benzo[1,2-b:4,5-b']dithiophene (0.111 mmol), tris(dibenzylideneacetone)dipalladium(0) (0.005 mmol), and tri(o-tolyl)phosphine (0.02 mmol). The reaction is heated, then cooled, then finally precipitated with methanol. Polymer C was then collected.

Polymer D

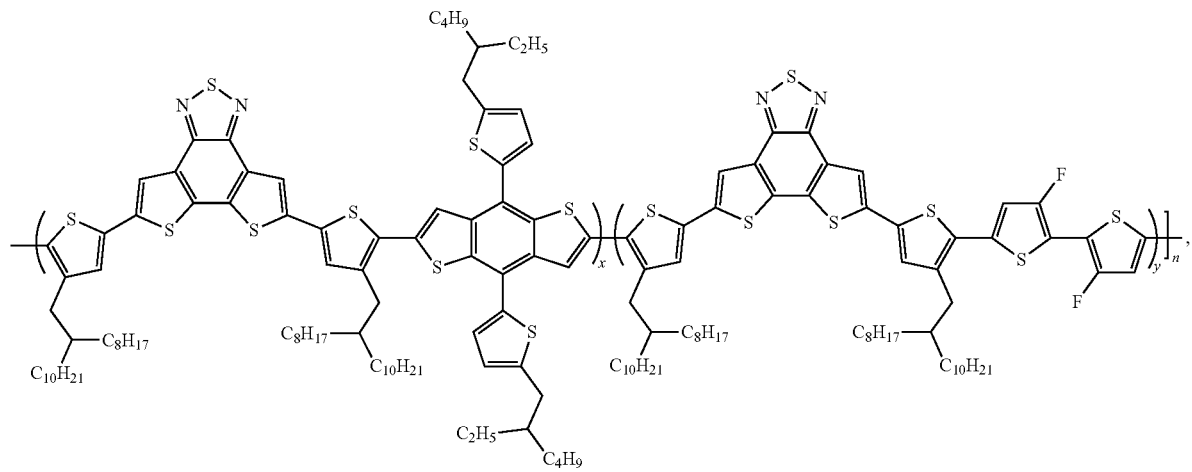

wherein x/y=60/40 is produced by combining compound 5 (0.088 mmol), 1,1'-(3,3'-Difluoro[2,2'-bithiophene]-5,5'-diyl)bis[1,1,1-trimethylstannane] (0.035 mmol), 4,8-Bis[5-(2-ethylhexyl)thien-2-yl]-2,6-bis(trimethylstannyl)benzo[1,2-b:4,5-b']dithiophene (0.053 mmol), tris(dibenzylideneacetone)dipalladium(0) (0.004 mmol), and tri(o-tolyl)phosphine (0.014 mmol). The reaction is heated, then cooled, then finally precipitated with methanol. Polymer D (0.084 mmol, 95% yield) was then collected.

Polymer E

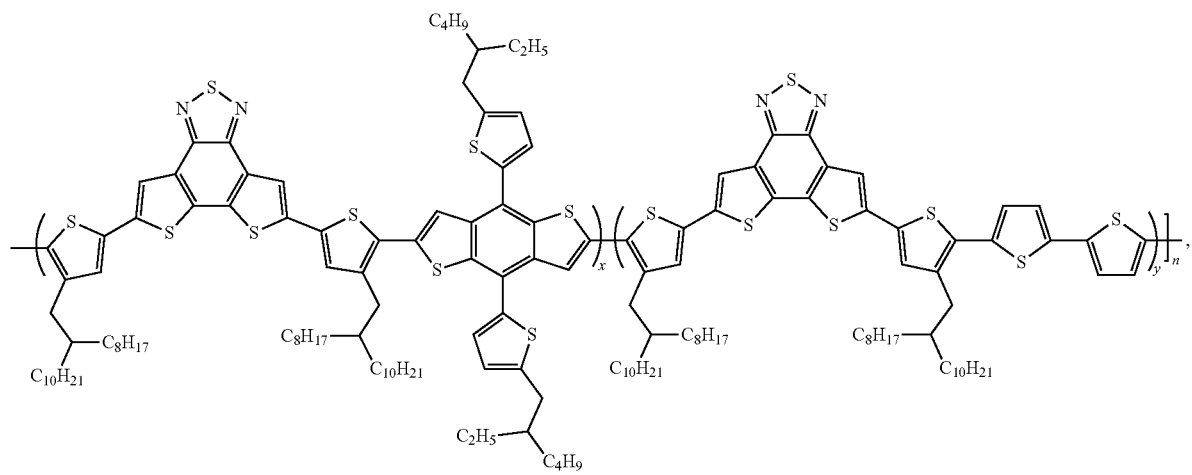

wherein x/y=50/50 is produced by combining compound 5 (0.13 mmol), 1,1'-[2,2'-Bithiophene]-5,5'-diylbis[1,1,1-trimethylstannane] (0.066 mmol), 4,8-Bis[5-(2-ethylhexyl)thien-2-yl]-2,6-bis(trimethylstannyl)benzo[1,2-b:4,5-b']dithiophene (0.066 mmol), tris(dibenzylideneacetone)dipalladium(0) (0.005 mmol), and tri(o-tolyl)phosphine (0.021 mmol). The reaction is heated, then cooled, then finally precipitated with methanol. Polymer E (0.105 mmol, 79% yield) was then collected.

Polymer F

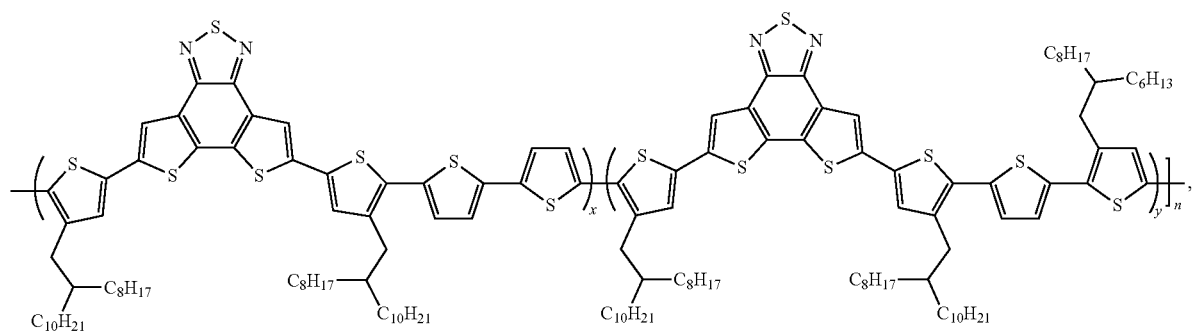

wherein x/y=80/20 is produced by combining compound 5 (0.15 mmol), 1,1'-[2,2'-Bithiophene]-5,5'-diylbis[1,1,1-trimethylstannane] (0.12 mmol), 1,1'-[3'-(2-Hexyldecyl)[2,2'-bithiophene]-5,5'-diyl]bis[1,1,1-trimethylstannane] (0.03 mmol), tris(dibenzylideneacetone)dipalladium(0) (0.006 mmol), and tri(o-tolyl)phosphine (0.024 mmol). The reaction is heated, then cooled, then finally precipitated with methanol. Polymer F (0.114 mmol, 76% yield) was then collected.

Polymer G

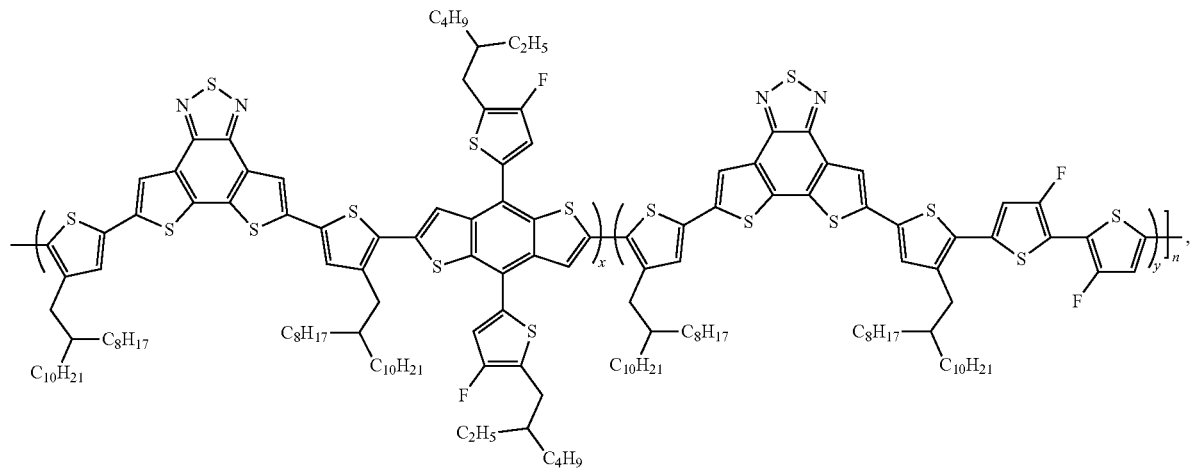

wherein x/y=50/50 is produced by combining compound 5 (0.124 mmol), 1,1'-(3,3'-Difluoro[2,2'-bithiophene]-5,5'-diyl)bis[1,1,1-trimethylstannane] (0.062 mmol), 1,1'-[4,8-Bis[5-(2-ethylhexyl)-4-fluoro-2-thienyl]benzo[1,2-b:4,5-b']dithiophene-2,6-diyl]bis[1,1,1-trimethylstannane] (0.062 mmol), tris(dibenzylideneacetone)dipalladium(0) (0.005 mmol), and tri(o-tolyl)phosphine (0.02 mmol). The reaction is heated, then cooled, then finally precipitated with methanol. Polymer G (0.116 mmol, 94% yield) was then collected.

Polymer H

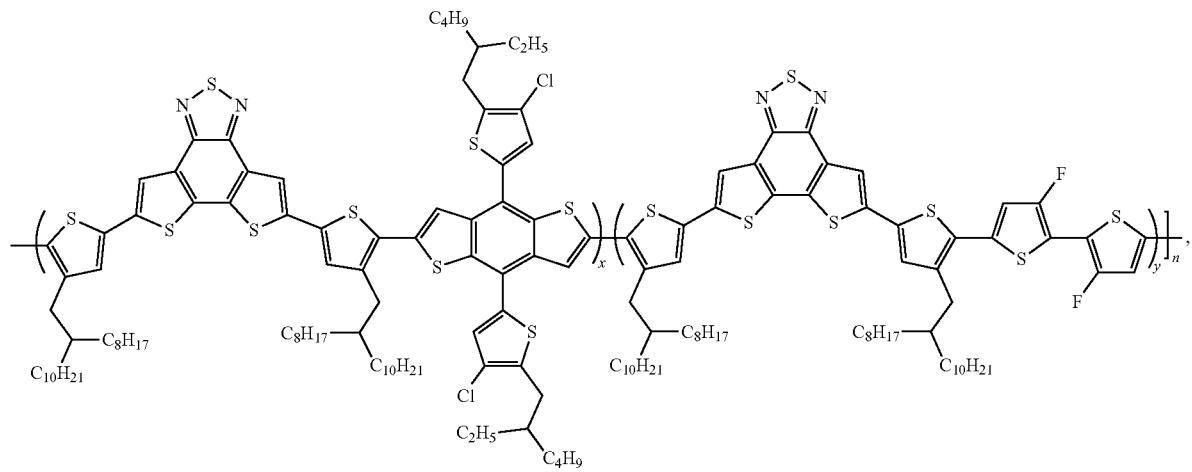

wherein x/y=50/50 is produced by combining compound 5 (0.088 mmol), 1,1'-(3,3'-Difluoro[2,2'-bithiophene]-5,5'-diyl)bis[1,1,1-trimethylstannane] (0.044 mmol), 1,1'-[4,8-Bis[4-chloro-5-(2-ethylhexyl)-2-thienyl]benzo[1,2-b:4,5-b']dithiophene-2,6-diyl]bis[1,1,1-trimethylstannane] (0.044 mmol), tris(dibenzylideneacetone)dipalladium(0) (3.2 mg, 0.004 mmol), and tri(o-tolyl)phosphine (0.014 mmol). The reaction is heated, then cooled, then finally precipitated with methanol. Polymer H (0.084 mmol, 95% yield) was then collected.

Polymer

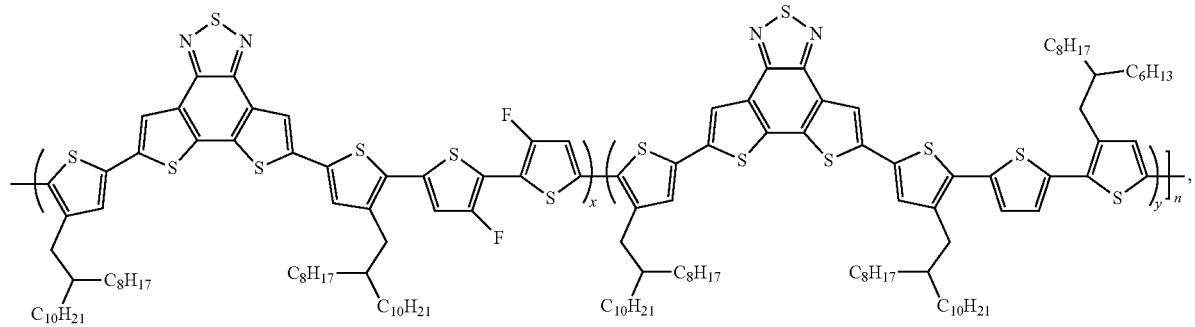

I wherein x/y=80/20 is produced by combining compound 5 (0.097 mmol), 1,1'-(3,3'-Difluoro[2,2'-bithiophene]-5,5'-diyl)bis[1,1,1-trimethylstannane] (0.078 mmol), 1,1'-[3'-(2-Hexyldecyl)[2,2'-bithiophene]-5,5'-diyl]bis[1,1,1-trimethylstannane] (0.019 mmol), tris(dibenzylideneacetone)dipalladium(0) (0.004 mmol), and tri(o-tolyl)phosphine (0.016 mmol). The reaction is heated, then cooled, then finally precipitated with methanol. Polymer I (0.083 mmol, 85% yield) was then collected.

Polymer

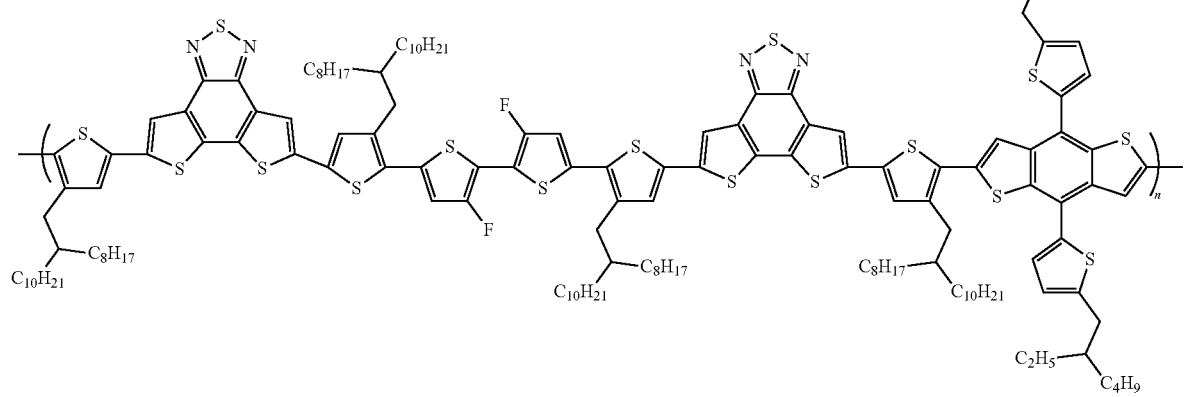

J is produced by combining compound 9 (0.044 mmol), 4,8-Bis[5-(2-ethylhexyl)thien-2-yl]-2,6-bis(trimethylstannyl)benzo[1,2-b:4,5-b']dithiophene (0.044 mmol), tris(dibenzylideneacetone)dipalladium(0) (0.002 mmol), and tri(o-tolyl)phosphine (0.007 mmol). The reaction is heated, then cooled, then finally precipitated with methanol. Polymer J (0.027 mmol, 61% yield) was then collected.

Anode

When used in as an organic photovoltaic device the polymer can be used in conjunction with an anode. The anode for the organic photovoltaic device can be any conventionally known anode capable of operating as an organic photovoltaic device. Examples of anodes that can be used include: indium tin oxide, aluminum, silver, carbon, graphite, graphene, PEDOT:PSS, copper, metal nanowires, $Zn_{99}InO_x$, $Zn_{98}In_2O_x$, $Zn_{97}In_3O_x$, $Zn_{95}Mg_5O_x$, $Zn_{90}Mg_{10}O_x$, and $Zn_{85}Mg_{15}O_x$.

Cathode

When used in as an organic photovoltaic device the polymer can be used in conjunction with a cathode. The cathode for the organic photovoltaic device can be any conventionally known cathode capable of operating as an organic photovoltaic device. Examples of cathodes that can be used include: indium tin oxide, carbon, graphite, graphene, PEDOT:PSS, copper, silver, aluminum, gold, metal nanowires.

Electron Transport Layer

When used in as an organic photovoltaic device the copolymer can be deposited onto an electron transport layer. Any commercially available electron transport layer can be used that is optimized for organic photovoltaic devices. In one embodiment the electron transport layer can comprise $(AO_x)_yBO_{(1-y)}$. In this embodiment, $(AO_x)$ and $BO_{(1-y)}$ are metal oxides. A and B can be different metals selected to achieve ideal electron transport layers. In one embodiment A can be aluminum, indium, zinc, tin, copper, nickel, cobalt, iron, ruthenium, rhodium, osmium, tungsten, magnesium, indium, vanadium, titanium and molybdenum.

In one embodiment B can be aluminum, indium, zinc, tin, copper, nickel, cobalt, iron, ruthenium, rhodium, osmium, tungsten, vanadium, titanium and molybdenum.

Examples of $(AO_x)_yBO_{(1-y)}$ include: $(SnO_x)_yZnO_{(1-y)}$, $(AlO_x)_yZnO_{(1-y)}$, $(AlO_x)_yInO_{z(1-y)}$, $(AlO_x)_ySnO_{z(1-y)}$, $(AlO_x)_yCuO_{z(1-y)}$, $(AlO_x)_yWO_{z(1-y)}$, $(InO_x)_yZnO_{(1-y)}$, $(InO_x)_ySnO_{z(1-y)}$, $(InO_x)_yNiO_{z(1-y)}$, $(ZnO_x)_yCuO_{z(1-y)}$, $(ZnO_x)_yNiO_{z(1-y)}$, $(ZnO_x)_yFeO_{z(1-y)}$, $(WO_x)_yVO_{z(1-y)}$, $(WO_x)_yTiO_{z(1-y)}$, and $(WO_x)_yMoO_{z(1-y)}$.

In an alternate embodiment, various fullerene dopants can be combined with $(AO_x)_yBO_{(1-y)}$ to make an electron transport layer for the organic photovoltaic device. Examples of fullerene dopants that can be combined include

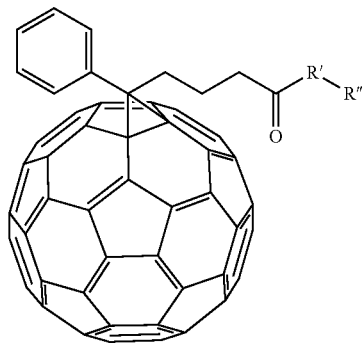

and [6,6]-phenyl-$C_{60}$-butyric-N-2-trimethylammonium ethyl ester iodide.

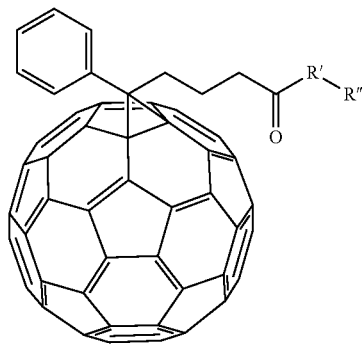

In the embodiment of R' can be selected from either N, O, S, C, or B. In other embodiment R" can be alkyl chains or substituted alkyl chains. Examples of substitutions for the substituted alkyl chains include halogens, N, Br, O, Si, or S.

In one example

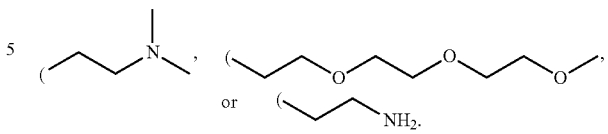

R" can be selected from Other examples of fullerene dopants that can be used include: [6,6]-phenyl-$C_{60}$-butyric-N-(2-aminoethyl)acetamide, [6,6]-phenyl-$C_{60}$-butyric-N-triethyleneglycol ester and [6,6]-phenyl-$C_{60}$-butyric-N-2-dimethylaminoethyl ester.

Organic Photovoltaic Device Fabrication

Zinc/tin oxide (ZTO):phenyl-C60-butyric-N-(2-hydroxyethyl)acetamide (PCBNOH) sol-gel solution was prepared by dissolving zinc acetate dihydrate or tin(II) acetate in 2-methoxyethanol and ethanolamine. Specifically, the ZTO: PCBNOH sol-gel electron transport layer solution was prepared by mixing Zn(OAc)$_2$ (3.98 g), Sn(OAc)$_2$ (398 mg) and PCBNOH (20.0 mg) in 2-methoxyethanol (54 mL) with ethanolamine (996 µL). Solutions were then further diluted to 65 vol % by adding more 2-methoxyethanol and stirred for at least an hour before spin casting onto indium tin oxide substrate to form the electron transport layer.

In alternate embodiments, the formation of ZTO ([6,6]-phenyl-$C_{60}$-butyric-N-2-trimethylammonium ethyl ester iodide (PCBNMI) can be used as well. One method of forming PCBNMI can be taking [6,6]-phenyl-C60-butyric-N-2-dimethylaminoethyl ester (0.05 g, 0.052 mmol) and dissolved it in dry THF (2 mL) under argon. Iodomethane (1.5 mL) was added in one portion and the vessel was sealed. The solution is then heated to 60° C. for 18 hours. The solution was cooled and opened to allow the liquids to evaporate. The solid residue was suspended in methanol, diluted with acetone, and centrifuged. This process was repeated to produce [6,6]-phenyl-C60-butyric-N-2-trimethylammonium ethyl ester iodide as a metallic green powder (0.05 g, ~99% yield).

The polymer and the acceptor, EH-IDTBR, in a ratio of 1:2 were dissolved in toluene at the concentration of 27 mg/mL to obtain the photo-active layer solution. The solution was stirred and heated at 80° C. overnight in a nitrogen filled glove box. The next day from about 0-0.5% vol % of 1,8-diiodooctane (DIO) was added before spin-coating of the photo-active layer.

Indium tin oxide patterned glass substrates were cleaned by successive ultra-sonications in acetone and isopropanol. Each 15 min step was repeated twice, and the freshly cleaned substrates were left to dry overnight at 60° C. Preceding fabrication, the substrates were further cleaned for 1.5 min in a UV-ozone chamber and the electron transport layer was immediately spin coated on top.

Sol-gel electron transport layer solution was filtered directly onto the indium tin oxide with a 0.25 µm poly (vinylidene fluoride) filter and spin cast at 4000 rpm for 40 s. Films were then annealed at 170° C. for 15 min, and directly transferred into a nitrogen filled glove box.

The photo-active layer was deposited on the electron transport layer via spin coating at 1600-4000 rpm for 40 s with the solution and the substrate being preheated at 80° C. and directly transferred into a glass petri dish for to be dried.

After drying, the substrates were loaded into the vacuum evaporator where MoO₃ (hole transport layer) and Ag (anode) were sequentially deposited by thermal evaporation. Deposition occurred at a pressure of <4×10' torr. MoO₃ and Ag had thicknesses of 5.0 nm and 120 nm, respectively. Samples were then encapsulated with glass using an epoxy binder and treated with UV light for 3 min.

Photovoltaic Device Performance

Cyclic Voltammetry Analysis

Cyclic voltammetry (CV) experiments were performed using a 3.0 mm diameter (7.06 mm2 area) glassy carbon working electrode, platinum coil counter electrode, and a silver wire/0.1M AgNO3 in acetonitrile reference solution. Solutions were purged of air using Argon preceding voltammetry measurements. Oxidation and reduction onset potentials were calculated as the intersection of the linear fits of the baseline current and the linear region of the oxidation or reduction event. Measurements with an initially positive scan direction at 100 mV/s were obtained on all solutions. Ferrocene was used as an external standard with an oxidation E1/2 of 0.136 V and a peak-to-peak separation of approximately 0.100 V. Small molecule material solutions were prepared at dilute concentrations of up to 1 mg/mL in a 0.3 M tetrabutylammonium hexafluorophosphate dichloromethane solution. A thin polymer film was coated from chlorobenzene onto the glassy carbon working electrode. Polymer films were measured in 0.1 M tetrabutylammonium hexafluorophosphate acetonitrile electrolyte. The HOMO levels were calculated from the CV oxidation onset potentials using equation 1. The polymer optical bandgap was derived from the onset of polymer film UV-visible absorption by using equation 2. The lowest un-occupied molecular orbital (LUMO) energy was calculated using equation 3.

$$E_{HOMO} = -[E_{ox(onset)} - E_{(1/2\ Ferrocene)} + 4.8]\ eV$$

$$E_{Bandgap} = [1240/\text{Onset Wavelength (nm)}]\ eV$$

$$E_{LUMO} = [E_{HOMO} + E_{Bandgap}]\ eV$$

$E_{ox(onset)}$ and $E_{red(onset)}$ are the onset oxidation and reduction potentials for the compounds against the ferrocene reference. The value −4.8 eV is the HOMO energy level of ferrocene against vacuum.

Device Fabrication

Small area OPV devices were fabricated with the inverted architecture ITO/ZnMOx/P:A/MoO₃/Ag.

Electron Transport Layer Deposition

Zinc tin oxide (ZTO) sol gel solutions were prepared by adding zinc acetate dihydrate (996 mg), tin (II) acetate (99.6 mg) to 2-methoxyethanol (10 mL) and ethanolamine (249 μL). Solutions were stirred for a minimum of 12 hours before use.

ITO patterned glass substrates were cleaned by successive 10 minutes ultra-sonication in detergent (Versa-Clean), deionized water, acetone, and isopropanol. The substrates were then cleaned for 1 minute 30 seconds in a UV-ozone chamber and the electron transport layer was immediately spin coated on the substrates. The ZTO sol gel solution was filtered directly onto ITO with a 0.25 μm poly(tetrafluoroethylene) filter and spin cast at 4,000 rpm for 40 seconds. Films were then annealed at 170° C. for 20 minutes, and directly transferred into a nitrogen filled glove box.

Photo-Active Layer Deposition

The photo-active layer was then coated from solution. The 1:(1-2) by wt. polymer:acceptor photo-active layer blends were prepared as 10-50 mg/mL solutions in toluene, chlorobenzene, or trimethylbenzene. Solutions were heated overnight at 80° C. Active layers were coated at 80-110° C. prior to coating. The hot solutions were deposited onto pre-heated ETL-coated substrates via spin coating at 1600-3000 rpm for 40 seconds. Following coating the films were solvent annealed for at least 1 hour or thermal annealed at 80-120° C. for 1-15 min.

Hole Transport Layer Deposition

After the photo-active layer anneal, the substrates were loaded under inert atmosphere into the vacuum evaporator where MoO3 (HTL) and Ag (the anode) were sequentially deposited by thermal evaporation. Deposition occurred at a pressure of 3×10-6 torr. MoO3 and Ag were deposited to a thickness of 6 nm and 120 nm, respectively. The deposition rate for the MoO3 was 0.1-0.6 Å/s and Ag was 1.1-1.7 Å/s. Samples were then sealed with the epoxy (EPO-TEK, OG116-31) and then cured in ELC-500 UV chamber for 3 minutes at room temperature before testing in air.

Device Testing

Cells were tested under AM 1.5G 100 mW/cm² conditions with a Newport Thermal Oriel 91192 1000 W solar simulator (4"×4" illumination size). The current density-voltage curves were measured using a Keithley 2400 source meter. The light intensity was calibrated with a crystalline silicon reference photovoltaic (area=0.4957 cm²) fitted with a KG-5 filter (calibrated by Newport to minimize spectral mismatch). Cells were masked and an active area of 0.0656 cm² was measured. Light soaking studies were performed on encapsulated devices installed with a UV filter with a 385 nm cutoff.

Table 1 below list the HOMO, LUMO, and Bandgap levels of polymers.

TABLE 1

| Polymer | HOMO (eV) | LITMO (eV) | Bandgap (eV) |
|---|---|---|---|
| Conventional Random Copolymer | −5.46 | −3.78 | −1.57 |
| Polymer A | −5.37 | −3.42 | −1.95 |
| Polymer B | −5.35 | −3.40 | −1.95 |
| Polymer D | −5.45 | −3.49 | −1.96 |
| Polymer E | −5.30 | −3.35 | −1.95 |
| Polymer F | −5.23 | −3.30 | −1.93 |
| Polymer G | −5.48 | −3.51 | −1.96 |
| Polymer H | −5.54 | −3.58 | −1.96 |
| Polymer I | −5.44 | −3.50 | −1.94 |
| Polymer J | −5.36 | −3.41 | −1.96 |

Table 2 below lists the OPV device performance for various polymer and acceptor blends.

TABLE 2

| Polymer | Acceptor | PCE | Voc | FF | Jsc |
|---|---|---|---|---|---|
| Conventional Random Copolymer | BTP-4Cl-12 | 10.4 | 0.786 | 69.2 | 19.2 |
| Polymer A | BTP-4Cl-12 | 12.5 | 0.797 | 66.7 | 23.5 |
| Polymer B | BTP-4Cl-12 | 10 | 0.805 | 62.6 | 19.9 |
| Polymer D | BTP-4Cl-12 | 10.7 | 0.803 | 64.6 | 20.6 |
| Polymer E | EH-IDTBR | 6.46 | 1.07 | 57.4 | 10.5 |
| Polymer E | BTP-4Cl-12 | 6.83 | 0.733 | 46.1 | 20.2 |
| Polymer F | EH-IDTBR | 5.48 | 0.919 | 50.3 | 11.9 |
| Polymer F | BTP-4Cl-12 | 7.54 | 0.684 | 54.5 | 20.3 |
| Polymer G | BTP-4Cl-12 | 9.63 | 0.845 | 60.2 | 18.9 |

TABLE 2-continued

| Polymer | Acceptor | PCE | Voc | FF | Jsc |
|---|---|---|---|---|---|
| Polymer H | BTP-4Cl-12 | 9.88 | 0.834 | 58.7 | 20.2 |
| Polymer J | BTP-4Cl-12 | 7.79 | 0.77 | 54.6 | 18.5 |

Jsc (mA/cm$^2$) Short-circuit current density (Jsc) is the current density that flows out of the solar cell at zero bias. Voc (V) Open-circuit voltage (Voc) is the voltage for which the current in the external circuit is zero. Fill factor percentage (FF %) is the ratio of the maximum power point divided by the open circuit voltage and the short circuit current. PCE (%) The power conversion efficiency (PCE) of a photovoltaic cell is the percentage of the solar energy shining on a photovoltaic device that is converted into usable electricity. EH-IDTBR is

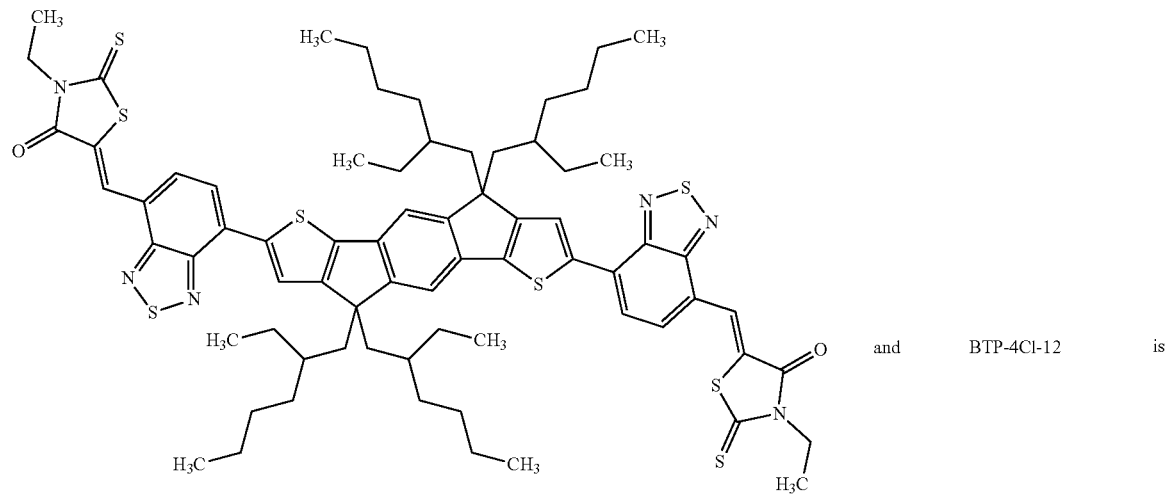

and BTP-4Cl-12 is

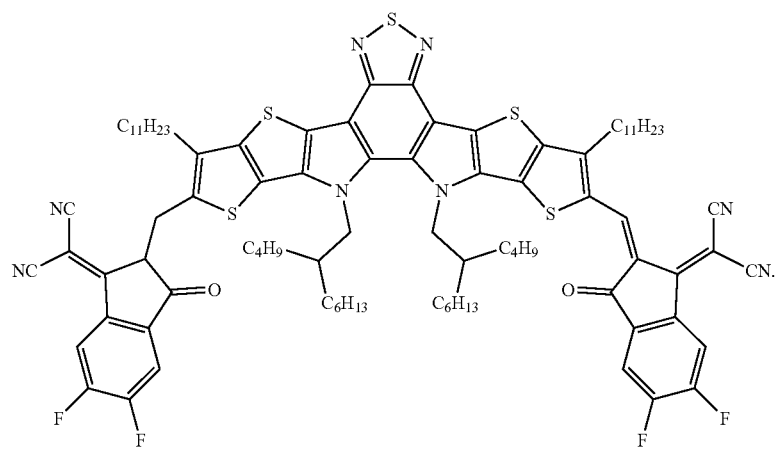

Table 3 below describes the light soaking stability of Polymer A:BTP-4Cl-12 blends in OPV devices.

TABLE 3

| Hours of Light Soaking | PCE (%) | FF (%) | Jsc (mA/cm2) | Voc (V) |
|---|---|---|---|---|
| 0 | 12.5 | 66.7 | 23.5 | 0.797 |
| 250 | 11.6 | 64.3 | 22.1 | 0.786 |

Figure 9:
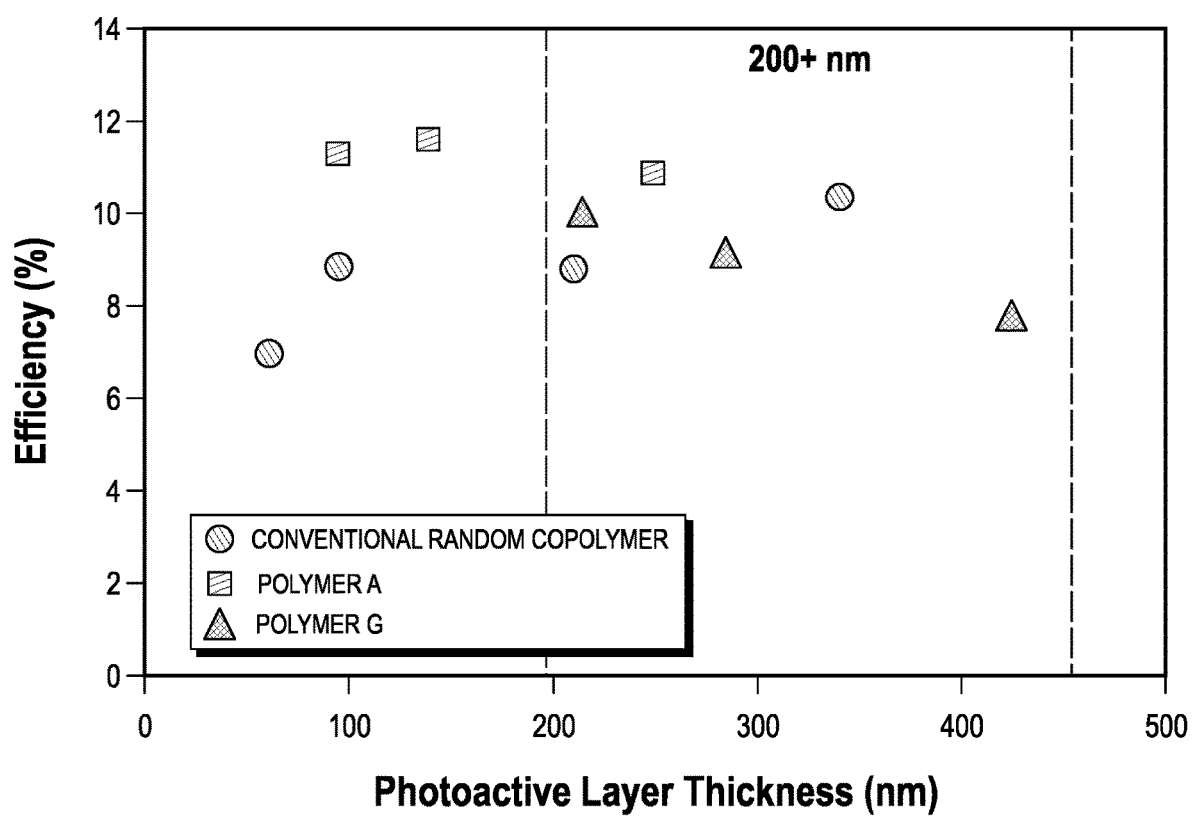
FIG. 9 below describes three different polymer blends in terms of slot die coating and thickness insensitivity.

FIG. 9 below describes three different polymer blends in terms of slot die coating and thickness insensitivity.

In closing, it should be noted that the discussion of any reference is not an admission that it is prior art to the present invention, especially any reference that may have a publication date after the priority date of this application. At the same time, each and every claim below is hereby incorporated into this detailed description or specification as an additional embodiment of the present invention.

Although the systems and processes described herein have been described in detail, it should be understood that various changes, substitutions, and alterations can be made without departing from the spirit and scope of the invention as defined by the following claims. Those skilled in the art may be able to study the preferred embodiments and identify other ways to practice the invention that are not exactly as described herein. It is the intent of the inventors that variations and equivalents of the invention are within the scope of the claims while the description, abstract and drawings are not to be used to limit the scope of the invention. The invention is specifically intended to be as broad as the claims below and their equivalents.

The invention claimed is:

1. A composition comprising:

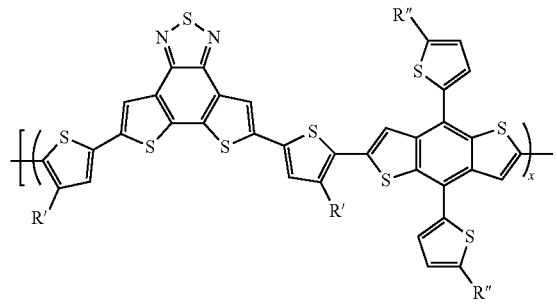

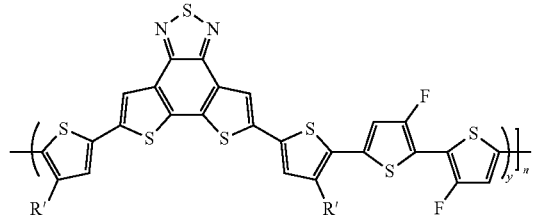

wherein the compositional ratio of x/y ranges from about 1/99 to about 99/1, and n ranges from 1 to 1,000,000, and wherein R' and R" are independently selected from: H, unsubstituted or substituted branched alkyls with 1 to 60 carbon atoms, or unsubstituted or substituted linear alkyls with 1 to 60 carbon atoms.

2. The composition of claim 1, wherein the composition is a photovoltaic material.

3. The composition of claim 1, wherein the composition is an active layer material.

4. The composition of claim 1, wherein the composition is a semi-conducting material.

5. The composition of claim 1, wherein the composition is a donor material blended with an acceptor material.

6. The composition of claim 1, wherein the compositional ratio of x/y ranges from about 10/90 to about 90/10.

7. The composition of claim 1, wherein the compositional ratio of x/y ranges from about 30/70 to about 90/10.

8. The composition of claim 1, wherein the composition is a random polymer.

9. A composition comprising:

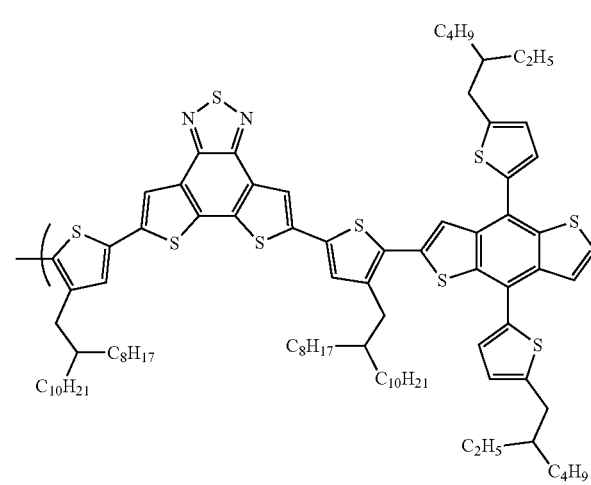
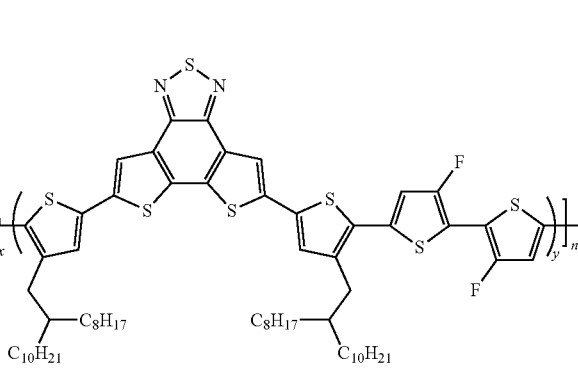

wherein the compositional ratio of x/y ranges from about 1/99 to about 99/1, and n ranges from 1 to 1,000,000, and wherein $R_1$ is selected from: H, unsubstituted or substituted branched alkyls with 1 to 60 carbon atoms, or unsubstituted or substituted linear alkyls with 1 to 60 carbon atoms.

10. The composition of claim 9, wherein the composition is a photovoltaic material.

11. The composition of claim 9, wherein the composition is an active layer material.

12. The composition of claim 9, wherein the composition is a semi-conducting material.

13. The composition of claim 9, wherein the composition is a donor material blended with an acceptor material.

14. The composition of claim 9, wherein the compositional ratio of x/y ranges from about 10/90 to about 90/10.

15. The composition of claim 9, wherein the compositional ratio of x/y ranges from about 30/70 to about 90/10.

16. The composition of claim 9, wherein the composition is a random polymer.

17. The composition of claim 9, wherein $R_1$ is selected from $C_6H_{13}$ and $C_{10}H_{21}$.

\* \* \* \* \*